United States Patent [19]

Slepian et al.

[11] Patent Number: 5,843,156
[45] Date of Patent: Dec. 1, 1998

[54] LOCAL POLYMERIC GEL CELLULAR THERAPY

[75] Inventors: Marvin Slepian; Stephen P. Massia, both of Tucson, Ariz.

[73] Assignee: Endoluminal Therapeutics, Inc., Tucson, Ariz.

[21] Appl. No.: 238,931

[22] Filed: May 6, 1994

Related U.S. Application Data

[63] Continuation-in-part of Ser. No. 132,745, Oct. 6, 1993, Pat. No. 5,575,815, which is a continuation-in-part of Ser. No. 118,978, Sep. 9, 1993, abandoned, which is a continuation-in-part of Ser. No. 987,357, Dec. 7, 1992, abandoned, which is a continuation of Ser. No. 857,700, Mar. 25, 1992, Pat. No. 5,213,580, which is a continuation of Ser. No. 593,302, Oct. 3, 1990, abandoned, which is a continuation of Ser. No. 235,998, Aug. 24, 1988, abandoned, which is a continuation-in-part of Ser. No. 182,516, Jan. 14, 1994, which is a continuation of Ser. No. 593,302, which is a continuation-in-part of Ser. No. 235,998, which is a continuation-in-part of Ser. No. 101,966, Aug. 4, 1993, Pat. No. 5,328,471, which is a continuation of Ser. No. 869,907, Apr. 15, 1992, abandoned, which is a continuation of Ser. No. 759,048, Sep. 5, 1991, abandoned, which is a continuation of Ser. No. 485,287, Feb. 26, 1990, abandoned.

[51] Int. Cl.[6] .................................. A61F 2/06; A61F 2/54
[52] U.S. Cl. .................................................. 623/1; 623/66
[58] Field of Search .................................. 673/1, 11, 12, 673/16; 604/96

[56] References Cited

U.S. PATENT DOCUMENTS

| | | | |
|---|---|---|---|
| 2,642,874 | 6/1953 | Keeling . | |
| 2,675,619 | 4/1954 | Cone ........................................... | 33/76 |
| 2,677,700 | 5/1954 | Jackson et al. .......................... | 260/488 |
| 2,854,982 | 10/1958 | Pagano . | |
| 2,979,578 | 4/1961 | Curtis ....................................... | 200/32 |
| 3,036,118 | 5/1962 | Jackson et al. .......................... | 260/484 |
| 3,535,307 | 10/1970 | Moss et al. ............................... | 260/209 |

(List continued on next page.)

FOREIGN PATENT DOCUMENTS

| | | |
|---|---|---|
| 0183372 | 6/1989 | European Pat. Off. . |
| 0 455 396 A1 | 11/1991 | European Pat. Off. . |
| WO 89/10155 | 11/1989 | WIPO . |
| WO 89/12478 | 12/1989 | WIPO . |
| WO 90/01969 | 3/1990 | WIPO . |
| WO 91/07154 | 5/1991 | WIPO . |
| PCT/US91/ 01242 | 9/1991 | WIPO . |
| WO 91/12846 | 9/1991 | WIPO . |
| WO93/01286 | 1/1993 | WIPO . |
| WO93/17669 | 9/1993 | WIPO . |
| WO93/24520 | 12/1993 | WIPO . |

OTHER PUBLICATIONS

Amaillay, Monique, et al., "The Cellular Interactions of Laminin Fragments," *J. Biol. Chem.* 262(24):11532–11538 (1987).

Boretos, "Improved Intravascular Delivery of Drug Via a Polyethylene Jet Catheter," The 13th Annual Meeting of the Society of *Biomaterials*, p. 128.

Clowes, Alexander W., et al., "Kinetics of Cellular Proliferation after Arterial Injury," Laboratory Investigation 49(3):327 (1983).

(List continued on next page.)

*Primary Examiner*—Debra S. Brittingham
*Attorney, Agent, or Firm*—Arnall Golden & Gregory, LLP

[57] ABSTRACT

A method for providing a synthetic barrier made of biocompatible polymeric materials in vivo which involves application of a material to a tissue or cellular surface such as the interior surface of a blood vessel, tissue lumen or other hollow space, is disclosed herein. The material may also be applied to tissue contacting surfaces of implantable medical devices. The polymeric materials are characterized by a fluent state which allows application to and, preferably adhesion to, tissue lumen surfaces, which can be increased or altered to a second less fluent state in situ; controlled permeability and degradability; and, in the preferred embodiments, incorporation of bioactive materials for release in vivo, either to the tissue lumen surface or to the interior of the lumen, which alter cell to cell interactions.

19 Claims, 7 Drawing Sheets

U.S. PATENT DOCUMENTS

| | | |
|---|---|---|
| 3,829,506 | 8/1974 | Schmolka et al. .................. 260/615 B |
| 3,868,956 | 3/1975 | Alfidi et al. . |
| 3,880,158 | 4/1975 | Gurney . |
| 3,987,000 | 10/1976 | Gleichenhagen et al. . |
| 4,140,126 | 2/1979 | Choudhury . |
| 4,156,067 | 5/1979 | Gould . |
| 4,188,373 | 2/1980 | Krezanoski ............................. 424/78 |
| 4,272,518 | 6/1981 | Moro et al. . |
| 4,377,010 | 3/1983 | Fydelor et al. . |
| 4,423,725 | 1/1984 | Baran et al. . |
| 4,445,892 | 5/1984 | Hussein et al. . |
| 4,448,188 | 5/1984 | Loeb . |
| 4,459,252 | 7/1984 | MacGregor . |
| 4,474,751 | 10/1984 | Haslam et al. ........................... 424/78 |
| 4,474,752 | 10/1984 | Haslam et al. ........................... 424/78 |
| 4,474,753 | 10/1984 | Haslam et al. ........................... 424/78 |
| 4,478,822 | 10/1984 | Haslam et al. ........................... 424/78 |
| 4,503,569 | 3/1985 | Dotter . |
| 4,517,686 | 5/1985 | Ruoslahti et al. ............................. 3/1 |
| 4,520,823 | 6/1985 | LeVeen et al. . |
| 4,553,545 | 11/1985 | Maass et al. . |
| 4,560,374 | 12/1985 | Hammerslag et al. .................. 604/49 |
| 4,573,966 | 3/1986 | Weikl et al. . |
| 4,578,079 | 3/1986 | Ruoslahti et al. ........................ 623/11 |
| 4,580,568 | 4/1986 | Glanturco . |
| 4,589,881 | 5/1986 | Pierschbacher et al. .................. 623/11 |
| 4,610,662 | 9/1986 | Weikl et al. . |
| 4,627,436 | 12/1986 | Leckrone ............................. 128/303.1 |
| 4,636,195 | 1/1987 | Wolinsky . |
| 4,650,466 | 3/1987 | Luther . |
| 4,655,746 | 4/1987 | Daniels et al. . |
| 4,655,771 | 4/1987 | Wallsten . |
| 4,674,506 | 6/1987 | Alcond . |
| 4,690,684 | 9/1987 | McGreevy et al. . |
| 4,701,509 | 10/1987 | Sun et al. . |
| 4,702,917 | 10/1987 | Schindler . |
| 4,733,665 | 3/1988 | Palmaz . |
| 4,744,366 | 5/1988 | Jang . |
| 4,754,752 | 7/1988 | Ginsburg et al. . |
| 4,763,653 | 8/1988 | Rockey .................................. 128/344 |
| 4,763,654 | 8/1988 | Jang . |
| 4,767,619 | 8/1988 | Murray ..................................... 424/78 |
| 4,771,777 | 9/1988 | Horzewski et al. . |
| 4,781,677 | 11/1988 | Wilcox . |
| 4,799,479 | 1/1989 | Spears . |
| 4,820,298 | 4/1989 | Leveen et al. . |
| 4,824,436 | 4/1989 | Wolinsky ................................ 604/53 |
| 4,832,688 | 5/1989 | Sagae et al. . |
| 4,861,760 | 8/1989 | Mazuel et al. ............................ 514/54 |
| 4,879,135 | 11/1989 | Greco et al. ................................ 623/1 |
| 4,883,660 | 11/1989 | Blackman et al. ........................ 424/78 |
| 4,911,926 | 3/1990 | Henry et al. ............................. 424/426 |
| 4,938,763 | 7/1990 | Dunn et al. . |
| 5,041,380 | 8/1991 | Ruoslahti et al. .................... 435/240.2 |
| 5,059,211 | 10/1991 | Stack et al. . |
| 5,092,841 | 3/1992 | Spears ....................................... 604/96 |
| 5,100,429 | 3/1992 | Sinofsky et al. ......................... 604/96 |
| 5,120,829 | 6/1992 | Pierschbacher et al. . |
| 5,126,141 | 6/1992 | Henry . |
| 5,135,751 | 8/1992 | Henry et al. ............................. 424/426 |
| 5,147,385 | 9/1992 | Beck et al. . |
| 5,149,780 | 9/1992 | Plow et al. .............................. 530/324 |
| 5,169,930 | 12/1992 | Ruoslahti et al. ...................... 530/350 |
| 5,171,217 | 12/1992 | March et al. . |
| 5,213,580 | 5/1993 | Slepian et al. ........................... 623/11 |
| 5,258,042 | 11/1993 | Mehta ...................................... 623/66 |
| 5,261,878 | 11/1993 | Galindo .................................... 604/96 |
| 5,306,249 | 4/1994 | Michel . |
| 5,306,250 | 4/1994 | March et al. . |
| 5,306,286 | 4/1994 | Stack et al. . |
| 5,328,470 | 7/1994 | Nabel et al. . |
| 5,399,352 | 3/1995 | Hanson .................................. 424/423 |

OTHER PUBLICATIONS

Clowes, Alexander W., et al., "Kinetics of Cellular Proliferation after Arterial Injury," *Laboratory Investigation* 52(6):611 (1985).

Clowes, Alexander W. and Stephen M. Schwartz, "Significance of Quiescent Smooth Muscle Migration in the Injured Rat Caro Artery," *Circulation Research* 56(1)139–145 (Jan. 1985).

Fogerty, Frances J., et al., "Inhibition of Binding of Fibronectin to Matrix Assembly Sites by Anti–Integrin ($\alpha$, $\beta$,) Antibodies," *J. Cell Biology*, 111:699–708 (1990).

Gahlsan, Kurt R., et al., "Inhibition of In Vitro Tumor Cell Invasion by Arg–Gly–Asp–containing Synthetic Peptides," *J. Cell Biol.* 106:925–930 (1988).

Ginsberg, Mark H., et al., "Cytoadhesins, Integrins, and Platelets," Thrombosis and Haemostasis 59(1);1–6 (1988).

Greene, T.W., and Wuts, P.G.M., Protective Groups in Organic Synthesis, 2d Ed., John Wiley & Sons, Inc., pp. 317–318 (1991).

Humphrias, Martin J., et al., "A Synthetic Peptide from Fibronactin Inhibits Experimental Matastasis of Murine Melanoma Cells," *Science* 233:467–470 (Jul. 1986).

Kerenyi, et al., "Local Enzymatic Treatment of Atherosclerotic Plaques," *Experimental and Molecular Pathology*, vol. 49, pp. 330–338 (1988).

McBride, et al., "Restenosis After Successful Coronary Angioplasty," *N. Eng. J. Med.*, pp. 1734–1737 (1988).

Pierschbacher, Michael and Erkki Runslahti, "Variants of the cell recognition site of fibronactin that retain attachment–promoting activity," *Proc. Natl. Sci.* 81:5985–5988 (Oct. 1984).

Phillips, David R., et al., The Platelet Membrane Glycoprotein llb–llla Complex, *Blood* 71(4):831–843 (Apr. 1988).

Ruoslahti, Erkki and Michael D. Pierschbacher, "New Perspectives Cell Adhesion; RGD and Integrins," *Science* 238:491–497 (Oct. 1987).

Vaheri, Antti, et al., "Codistribution of pericellular matrix proteins in cultured fibroblasts and loss in transformation: Fibronectin and procollagen," *Proc. Natl. Acad Sci.* 75(10):4944–4948 (Oct. 1978).

"Controlled Release Systems: Fabrication Technology" vol. II, Dean Hsieh, Editor, Chapter 3 Gels for Drug Delivery by David W. Woodford and Dean S. T. Hsieh pp. 42–57 (CRC Press, Florida).

"The Molecular and Cellular Biology of Wound Repair" ed. R.A.F. Clark and P. M. Henson ed., (Plenum Press, NY 1988) Chapter 13. J.B. McCarthy, Sas, and Furcht*.

Aumailley, Monique, "Arg–Gly–Asp constrained within cyclic pentapeptides," *FEBS* 29(1):50–54 (1991).

Varki, Ajit P., et al., "Identification of a variant of mucolipidosis III (pseudo Hurler polydystrophy); A catalytically active N–acetylglucosaminyl–hosphotransferase that fails to phosphorylate lysosomal enzymes," *Proc. Natl. Acad. Sci. USA* 78:7773–7777 (1981).

Choi, Eric T., et al., "Inhibition of neointimal hyperplasia by blocking $\alpha$, $\beta_2$ integrin with a small peptide antagonist GpenGRGDSPCA," *J. Vascular Surgery* 125–134 91994).

Greene, T.W., and Wuts, P.G.M., Protective Groups in Organic Synthesis, 2d Ed., John Wiley & Sons, Inc., pp. 317–318 (1991)*.

Gurrath, Marion, et al., "Conformation/activity studies of rationally designed potent anti-adhesive RGD peptides," *FEBS* 210:911–921 (1992).

Mohri, Hiroshi, et al., "Novel Effect of Cyclicization of the Arg–Gly–Asp–Containing Peptide on Vitronectin Binding to Platelets," *American Journal of Hematology* 37:14–19 (1991).

Naito, Michitaka, et al., "Vitronectin–Induced Haptotaxis of Vascular Smooth Muscle Cells In Vitro," *Experimental Cell Research* 194:154–156 (1991).

Pierschbacher and Erkki Ruoslahti, "Influence of Sterochemistry of the Sequence Arg–Gly–Asp–Xaa on Binding Specificity in Cell Adhesion," *J. Biol. Chem.* 262(36):17294–17298 (1987).

Scarborough, Robert M., et al., "Design of Potent and Specific Integrin Antagonists," *J. Biol. Chem.* 268(2):1066–1073 (1993).

Tay, Merrill, Salzman and Lindon, *Biomaterials* 10:11–15 (1989).

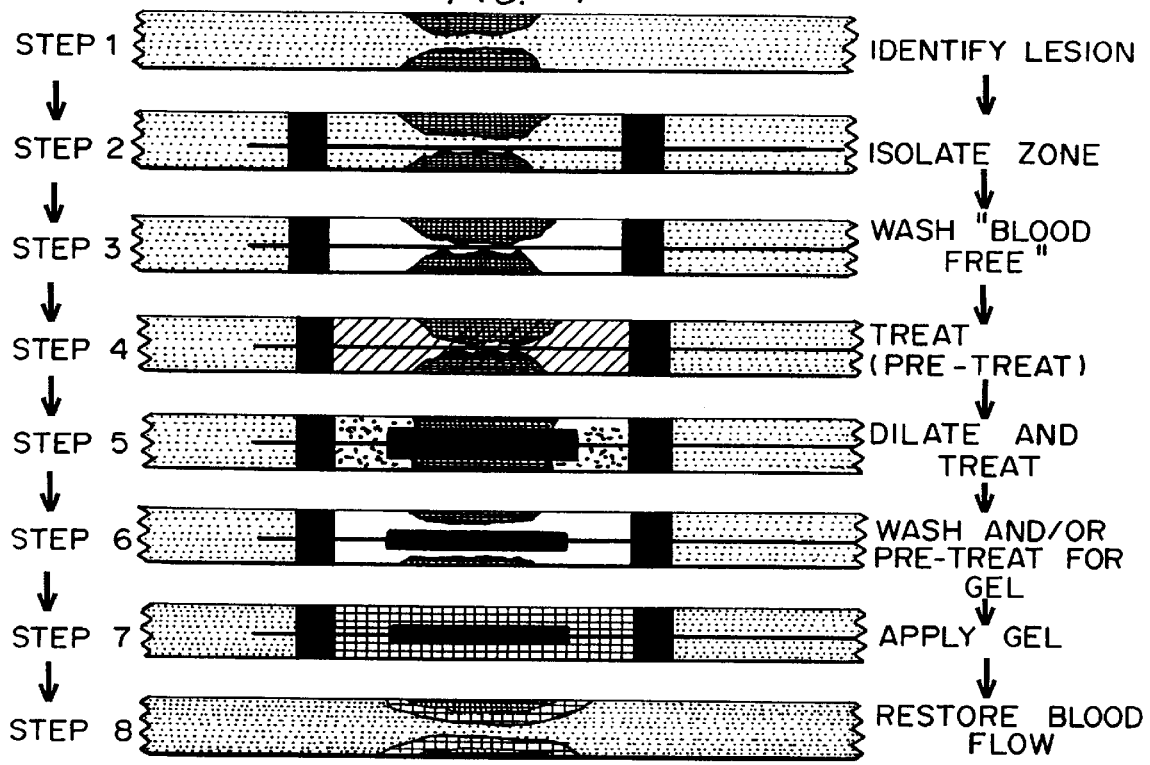
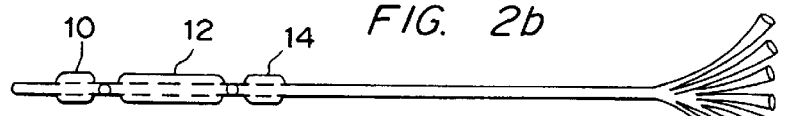
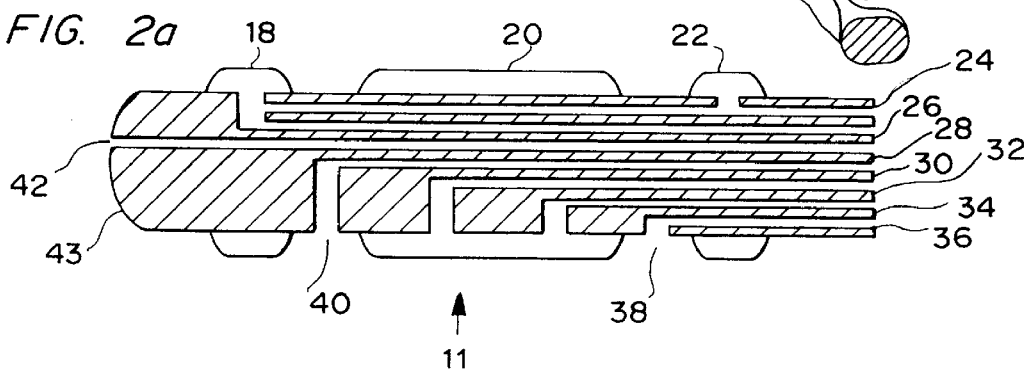
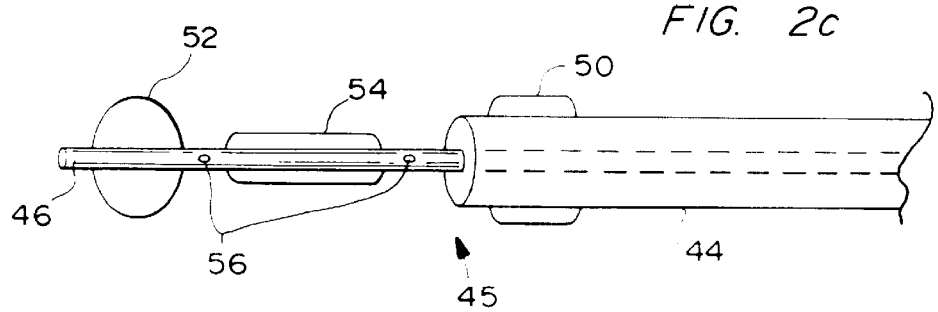

LOCAL POLYMERIC GEL CELLULAR THERAPY

This application is a continuation-in-part of U.S. Ser. No. 08/132,745, filed Oct. 6, 1993, now U.S. Pat. No. 5,575,815, which is a continuation-in-part of U.S. application Ser. No. 08/118,978, filed Sep. 9, 1993, now abandoned, which is a continuation-in-part of U.S. application Ser. No. 07/987,357, filed Dec. 7, 1992, now abandoned, which is a continuation of U.S. application Ser. No. 07/857,700, filed Mar. 25, 1992, now U.S. Pat. No. 5,213,580 which is a continuation of U.S. application Ser. No. 07/593,302, filed Oct. 3, 1990, now abandoned, which is a continuation of U.S. application Ser. No. 07/235,998, filed Aug. 24, 1988, now abandoned, and which is a continuation-in-part of U.S. application Ser. No. 08/182,516, filed Jan. 14, 1994, still pending, which is a continuation of U.S. application Ser. No. 07/593,302, filed Oct. 3, 1990, now abandoned, which is a continuation-in-part of U.S. Ser. No. 07/235,998, filed Aug. 24, 1988, now abandoned, and which is also a continuation-in-part of U.S. application Ser. No. 08/101,966, filed Aug. 4, 1993, now U.S. Pat. No. 5,328,471, which is a continuation of U.S. application Ser. No. 07/869,907, filed Apr. 15, 1992, now abandoned, which is a continuation of U.S. application Ser. No. 07/759,048, filed Sep. 5, 1991, now abandoned, which is a continuation of U.S. application Ser. No. 07/485,287, filed Feb. 26, 1990, now abandoned.

BACKGROUND OF THE INVENTION

This invention is generally in the area of methods of treating tissue defects and modulating cell to cell interactions by administration of a polymeric gel material containing bioactive molecules to a tissue surface.

The hollow or tubular geometry of organs commonly has functional significance, for example, in the facilitation of fluid or gas transport (blood, urine, lymph, oxygen or respiratory gasses) or cellular containment (ova, sperm). Disease processes may affect organ tissue or its components by encroaching upon, obstructing or otherwise reducing the cross-sectional areas of the hollow or tubular elements. Additionally, other disease processes may violate the native boundaries of the hollow organ and thereby affect its barrier function and/or containment ability. These disease processes include those which are induced by aging, diet, injury, or activation of the coagulation, complement and other inflammatory systems or the development of a neoplasia or malignancy. The ability of the organ or structure to properly function can then be severely compromised. This is particular evident in coronary artery disease, where successful treatment initial may subsequently be complicated by overproliferation of endothelium, called restenosis, or vessel renarrowing or closing after dilation.

The types of problems associated with angioplasty are also characteristic of similar treatment of other types of natural lumens, including surgical correction and balloon dilation of urinary and reproductive tract disorders, for example, following prostate surgery, or treatment by laparoscopy of the fallopian tubes, as well as treatment of openings arising from disease, surgery and trauma. Further, these reobstructive problems also occur in artificially or therapeutically created lumens or pathways, such as in renarrowing of the intrahepatic shunt formed in transjugular intrahepatic portosystemic shunting procedure (TIPS).

As described in the literature, for example, U.S. Pat. No. 5,213,580 to Slepian, pre-formed polymeric materials can be inserted into blood vessels and then contoured to fit the surfaces of the vessels, providing protection of the blood vessel and prevention of restenosis. As described in U.S. Pat. Nos. 5,126,141 and 5,135,751 to Henry, et al., aqueous, thermally reversible gel compositions formed of a polyoxyalkylene polymer and an ionic polysaccharide can be applied to injured areas of the body to prevent adhesions. These same type of polyoxyalkylene polymers have also been used for the local delivery of oligonucleotides (antisense) to the surgically exposed surface of blood vessels for treatment of restenosis, as described by WO93/01286 by Rosenberg, et al.

None of these, however, describe a means for forming a polymeric material at or on a lumen surface which can be used as a barrier of controlled permeability or for controlled delivery of a bioactive substance, nor can these materials be targeted to a particular cell type. While the prior art discloses useful treatments of damaged lumen surfaces, it would be desirable to have materials which could provide these additional useful functions, especially controlled permeability which would allow free exchange of gases and nutrients or controlled diffusion of macromolecules which are beneficial to the lumen surface, as well as for controlled drug delivery to the surface, for example, of growth factors or antiinflammatories.

It is therefore an object of the present invention to provide polymeric materials which are initially amorphous, biocompatible, and can be formed in situ.

It is a further object of the present invention to provide polymeric materials of controlled permeability which can be used as selective barriers on lumen surfaces.

It is a still further object of the present invention to provide materials which can be used for controlled delivery of drugs and other biologically active substances, either to tissue lumen surfaces or into the lumens themselves.

SUMMARY OF THE INVENTION

Methods for creating in situ specific local interactions of cellular interactions in living tissue are disclosed. This is accomplished by applying a fluent material which forms a local, selectively permeable barrier, alone or in combination with specific bioactive molecules, directly to a site to be treated. Upon application, the fluent material is conformed to the tissue and converted to a less fluent state by alteration in temperature, ion concentration, application of shear force, or chemical or physical polymerization or crosslinking. In one embodiment, cellular interactions, such as formation of thrombus, inflammation, or adhesions, are inhibited by physically blocking cellular and/or macromolecular interactions while allowing selective permeability to nutrients, gases, and other molecules. Permeability is controlled by selection of the material, method of manufacture, density, degree of crosslinking, molecular weight of monomer units, incorporation of particulate or other material, and degradability or non-biodegradability of the polymeric material. In another embodiment, the polymeric gel is provided in combination with bioactive molecules, especially those providing contact guidance, or chemotactic or haptotactic activity, which can be utilized to alter cell proliferation, migration, and inflammatory reactions.

As demonstrated by the examples, a synthetic barrier made of a biocompatible polymeric material can be applied in vivo to a tissue or cellular surface such as the interior surface of a blood vessel or tissue lumen. The material may also be applied to tissue contacting surfaces of implantable medical devices. The polymeric material is applied in the first fluent state to the site to be treated using, for example, a catheter, or by means of spraying or irrigation at the time of surgery. The material is then reconfigured to have intimate conforming contact with the surface to be coated, and then maintained under conditions which convert the material into its second non-fluent state. The conversion may be achieved either by active methods in which the environment surrounding the material is altered by the addition or removal of chemicals or energy, or it may be by passive means in which, for example, maintaining the material at the normal internal body temperature of the patient causes the material to undergo conversion into its non-fluent state. The transition of the material from a fluent state to a non-fluent state may be the result of a phase change in which the material goes from a liquid state to a solid state, by gelation, or in the alternative, it may be the result of a viscosity change with the material actually remaining in a single phase.

BRIEF DESCRIPTION OF THE DRAWINGS

FIG. 1 is a schematic of the method of the present invention.

FIG. 2A is a cross sectional view of the multilumen features of the catheter shown in FIG. 2B. FIGS. 2B and 2C are expanded views of catheters useful in the method described herein for application of polymeric materials to the tissue lumen surfaces.

FIGS. 3A and 3B are photographs of the catheter and the catheter being inserted into the tube; FIG. 3C is of the two balloons in the catheter being inflated to seal off the vessel; FIG. 3D is of the polymeric material being injected into the tube; FIG. 3E is of the tube with the polymeric material having gelled and the balloons deflated; FIG. 3F is of the catheter being removed to leave a gel coating on the vessel walls with an interior lumen or annual space; and FIG. 3G is of the lumen after the balloons are collapsed and withdrawn from the coated vessel, and the material has been smoothed and thinned by reapplication of the distal occlusion balloon.

FIG. 6A is the control balloon abraded rat intimal (endoluminal) surface with significant platelet, white cell and fibrin deposition; FIG. 6B is the gel coated (Pluronic F127, 25% w/v) arterial surface showing a significant reduction in platelet, white cell and fibrin deposition and adherence.

DETAILED DESCRIPTION OF THE INVENTION

Figures 3A, 3B, 3C, 3D, 3E, 3F, 3G:
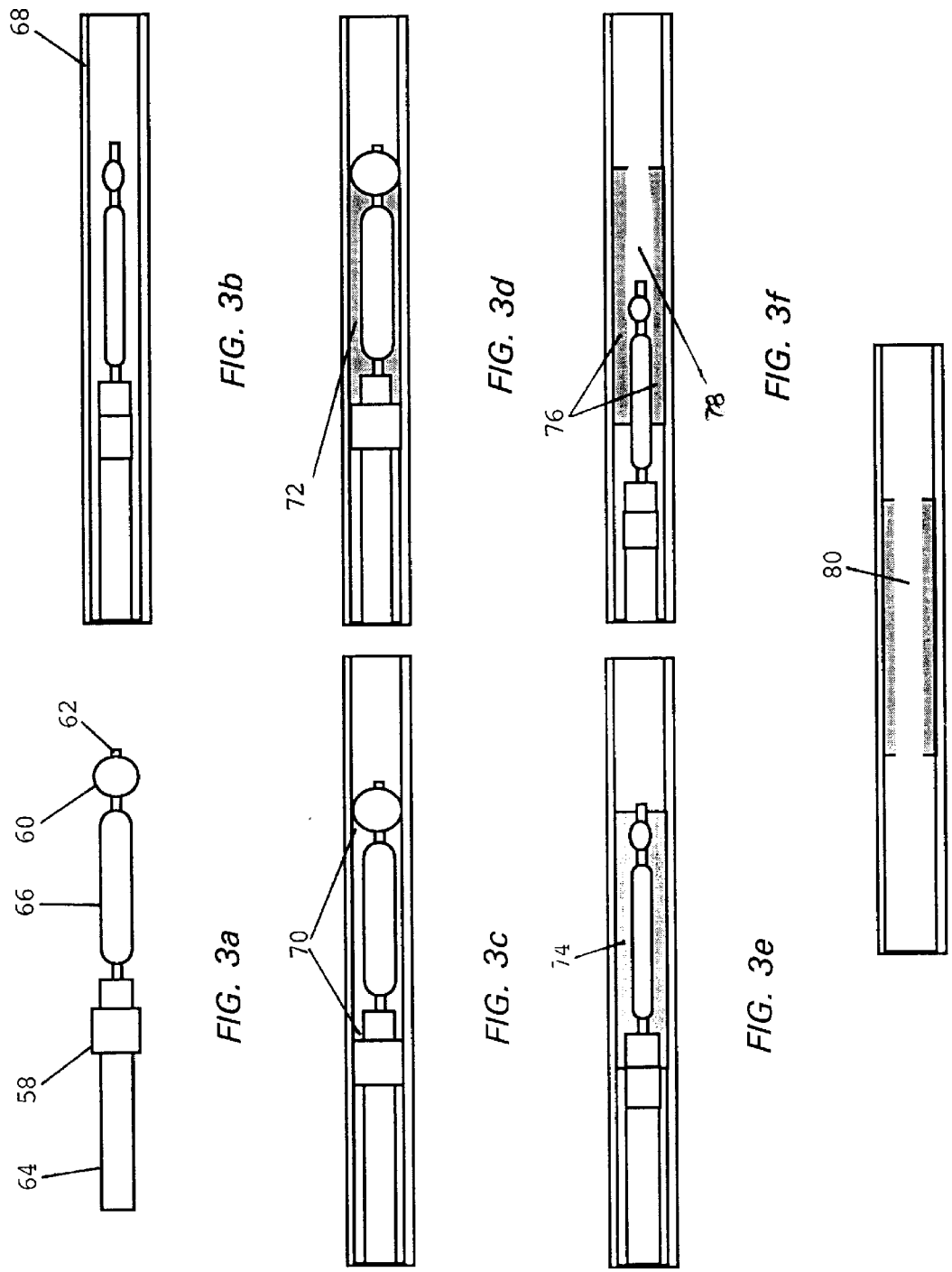
FIGS. 3A–3G are schematics of photographs of application of a polymeric material as described herein within a mock hollow tubular organ.

As described herein, polymeric materials are applied to the surface of tissue lumens to provide a barrier having either a controlled permeability to materials in the lumen, for example blood, and/or controlled release of incorporated bioactive agents.

Selection of Polymeric Materials

The basic requirements for the polymeric material are biocompatibility and the capacity to be applied in a fluent state then chemically or physically reconfigured under conditions which can be achieved in vivo to yield a non-fluent polymeric material having defined characteristics in terms of permeability and release of incorporated materials.

The polymeric materials can be applied as monomers, macromers, polymers, or combinations thereof, maintained as solutions, suspensions, or dispersions, referred to herein jointly as "solutions" unless otherwise stated. Although capable of many forms in their non-fluent state, organogels and hydrogels represent preferred embodiments. Although non-degradable and biodegradable materials can be used, biodegradable materials are preferred. As used herein, "biodegradable" is intended to describe materials that are non-permanent and removed by natural or imposed therapeutic biological and/or chemical processes. For application to the interior of blood vessels following angioplasty, it is preferred to use polymers degrading substantially six months after implantation; for prevention of adhesions or controlled release following treatment for injury or surgery, the degradation should be correlated with the time required for healing, i.e., generally in excess of six days but less than six months.

The polymeric materials are selected from those materials which can be polymerized or their viscosity altered in vivo by application of exogenous means, for example, by application of light, ultrasound, radiation, or chelation, alone or in the presence of added catalyst, or by endogenous means, for example, a change to physiological pH, diffusion of calcium ions (alginate) or borate ions (polyvinyl alcohol) into the polymer, or change in temperature to body temperature (37° C.).

As used herein, a hydrogel is defined as an aqueous phase with an interlaced polymeric component, with at least 60%, preferably at least 75%, more preferably with 80% or more, and as a specific example, with 90% of its weight as water. The following definition is from the Dictionary of Chemical Terms, 4th Ed., McGraw Hill (1989): Hydrogel: a colloid in which the disperse phase (colloid) has combined with the continuous phase (water) to produce a viscous jellylike product, for example, coagulated silicic acid.

An organogel is defined as an organic phase with an interlaced polymeric component, with at least 60%, preferably at least 75%, more preferably with 80% or more, and as a specific example, with 90% of its weight as organic solvent. Preferred solvents include non-toxic organic solvents, including but not limited to dimethyl sulfoxide (DMSO), and mineral and vegetable oils.

Suitable materials are commercially available or readily synthesizable using methods known to those skilled in the art. These materials include:

1. Materials which polymerize or alter viscosity as a function of temperature or shear or other physical forces.

Poly(oxyalkylene) polymers and copolymers such as poly (ethylene oxide)-poly(propylene oxide) (PEO-PPO) or poly (ethylene oxide)-poly(butylene oxide) (PEO-PBO) copolymers, and copolymers and blends of these polymers with polymers such as poly(alphahydroxy acids), including but not limited to lactic, glycolic and hydroxybutyric acids, polycaprolactones, and polyvalerolactones, can be synthesized or commercially obtained. For example, polyoxyalkylene copolymers are described by U.S. Pat. Nos. 3,829,506; 3,535,307; 3,036,118; 2,979,578; 2,677,700; and 2,675,619, the teachings of which are incorporated herein.

Polyoxyalkylene copolymers are sold by BASF and others under the tradename Pluronics™. Preferred materials include F-127, F-108, and for mixtures with other gel materials, F-67. These materials are applied as viscous solutions at room temperature or lower which solidify at the higher body temperature.

Other materials with this behavior are known in the art, and can be utilized as described herein. These include Klucel™ (hydroxypropyl cellulose), and purified konjac glucomannan gum.

Polymer solutions that are liquid at an elevated temperature but solid or gelled at body temperature can also be utilized. A variety of thermoreversible polymers are known, including natural gel-forming materials such as agarose, agar, furcellaran, beta-carrageenan, beta-1,3-glucans such as curdlan, gelatin, or polyoxyalkylene containing compounds, as described above. Specific examples include thermosetting biodegradable polymers for in vivo use described in U.S. Pat. No. 4,938,763 to Dunn, et al., the teachings of which are incorporated herein.

Thixotropic and pseudoplastic polymers exhibit shear thinning, whereby the polymer becomes more fluent under shear, and then reverts to a high-viscosity or gelled form on cessation of shear. A preferred example of a material altering viscosity from a liquid to a gel upon exposure to shear or other physical forces is the naturally occurring hyaluronic acid, most preferably of a high molecular weight in the range of 300,000 daltons or more, at concentrations of about 1% or more. Hyaluronic is present in joints where it acts to absorb shock and lubricate the moving surfaces. This can also be crosslinked ionically, as discussed below.

2. Materials which polymerize in the presence of ions or removal of ions.

Tissue and blood contain numerous anions and cations, at regulated conditions of pH, ionic strength and osmolarity, which can induce the gelation or local precipitation of polymers. Several divalent ions including calcium, barium, magnesium, copper, and iron are normal constituents of the body tissues and blood. These ions can be used to ionically crosslink polymers, for example, alginates and derivatized alginates and kappa, lambda, and iota carrageenans will gel in the presence of calcium ions. Other carboxylated and sulfated polymers such as hyaluronic acid, heparin, carboxymethyl cellulose, cellulose sulfate, xanthan gum, and pectin and various natural gums such as traganth, can substantially increase in viscosity in the presence of divalent cations. Monovalent ions can gel gellan; potassium can gel kappa carrageenan. Chitosan is soluble in mildly acidic conditions, and will gel at physiological pH or with phosphate or sulfate ions. Organogels can also be formed using these procedures. Typically the gelling polymer is dissolved in a tissue-compatible non-aqueous solvent and applied to tissue, where the polymers gels or precipitates as the organic solvent is removed by diffusion.

Materials which form polymers upon removal of ions, such as the salts of certain monomers or polymers, can also be used, where the salt diffuses or is diffused out of the monomer solution at the time of application to the tissue to be treated, or by addition of chelators such as ethylenediaminetetraacetic acid, EDTA, a chelating agent used to as an anticoagulant.

3. Materials that can be crosslinked chemically or with light, ultrasound or radiation.

Materials that can be crosslinked using light, ultrasound or radiation will generally be those materials which contain a double (ethylenic) bond or triple (acetylenic) bond, preferably with an electron withdrawing substituent attached to the double or triple bond, referred to inclusively herein as "unsaturated". Examples of suitable materials small molecules containing acrylic, allylic or vinyl groups, such as acrylic acid, vinyl acetate, vinyl pyrrolidone, allyl alcohol, and dimeric or oligomeric forms of these compounds such as methylene bisacrylamide. Preferred monomers are sufficiently large in molecular weight so as to not penetrate cells, typically 400 m.w., thereby minimizing toxicity. These include unsaturated derivatives of proteins, polysaccharides, or synthetic polymers. Biodegradable or non-biodegradable monomers may be used to form the polymer. Examples of suitable materials are described in WO93/17669 by Hubbell, et al., and U.S. Pat. No. 4,938,763 to Dunn, et al., the teachings of which are incorporated herein. Examples of preferred materials include the monomers which are polymerized into poly(acrylic acids) (i.e., Carbopols™), poly (acrylates), polyacrylamides, polyvinyl alcohols, polyethylene glycols, and ethylene vinyl acetates.

Photopolymerization can be achieved directly by high energy photons provided, for example, ultraviolet, x-ray, or gamma radiation, however agents which damage cells, typically ultraviolet less than 350 nm and gamma radiation, are to be avoided. Photopolymerization in visible light normally requires the presence of a photosensitizer, a substance that either increases the rate of photoinitiated polymerization or shifts the wavelength at which polymerization occurs. Photoinitiation has advantages since can be used to limit the thickness of the gel formed by photopolymerization to a thin membrane.

4. Materials that can be crosslinked by addition of covalent crosslinking agents such as glutaraldehyde.

Any amino containing polymer can be covalently crosslinked using a dialdehyde such as glutaraldehyde, or succindialdehyde, or carbodiimide (CDI). Examples of useful amino containing polymers include polypeptides and proteins such as albumin, elastin, and collagen, and polyethyleneimine. Peptides having specialized function, as described below, can also be covalently bound to these materials, for example, using crosslinking agents, during polymerization.

Any of the foregoing materials can be mixed with other materials to improve their physiological compatibility. These materials include buffers, physiological salts, conventional thickeners or viscosity modifying agents, fillers such as silica and cellulosics, and other known additives of similar function, depending on the specific tissue to which the material is to be applied.

Determination of Permeability of Polymeric Materials

The polymeric material is designed to achieve a controlled permeability, either for control of materials within the lumen or for release of incorporated materials. There are basically three situations that the polymeric material is designed to achieve with respect to materials present in the lumen: wherein there is essentially passage of only nutrients (small molecular weight compounds) and gases from the lumen through the polymeric material to the tissue lumen surface; wherein there is passage of nutrients, gases and selected macromolecules, including proteins and peptides; and wherein there is passage of nutrients, gases, macromolecules and cells. The molecular weight ranges of these materials are known and can therefore be used to calculate the desired porosity. For example, a macromolecule can be defined as having a molecular weight of greater than 1000 daltons; cells generally range from 600–700 nm to 10 microns, with aggregates of 30–40 microns in size.

Solidification of polymeric material, by gelation, viscosity change, phase change or polymerization, is generally referred to as "solidification" and yielding a "solidified material". Methods of achieving porosity control in the solidified material are known in the art. An excellent review of controlled release systems and fabrication technology is provided in "Controlled Release Systems: Fabrication Technology" Vol. II, Dean Hsieh, Editor, Chapter 3 "Gels for Drug Delivery" by David W. Woodford and Dean S. T. Hsieh pp. 42–57 (CRC Press, Florida), the teachings of which are incorporated herein.

Typically, porosity control is achieved by selection of the material to be solidified, i.e., chemical composition, molecular weight, availability of groups for crosslinking; the degree of crosslinking of the polymer: ionic strength, osmolarity and pH of the polymer solution; addition of viscosity modifying agents such as sorbitol, glycerin or sucrose; addition of lipids or highly charged polymers to alter surface binding to cells and proteins; and incorporation of water-insoluble organic material or particles. The latter can be used to form composites that have increased strength or form a gradient sieve.

Polymeric material can also be applied in layer of different or gradient porosity, or encapsulating bioactive materials, in the same or staggered layers for cyclic release. Release of incorporated biologically active materials is described below in more detail.

Incorporation of Bioactive Agents
1. Selection of Bioactive Agents

A wide variety of bioactive agents can be incorporated into the polymeric material. These can be physically or chemically incorporated into the polymeric material. Release of the physically incorporated material is achieved by diffusion and/or degradation of the polymeric material; release of the chemically incorporated material is achieved by degradation of the polymer or of a chemical link coupling the agent to the polymer, for example, a peptide which is cleaved in vivo by an enzyme such as trypsin, thrombin or collagenase. In some cases, it may be desirable for the bioactive agent to remain associated with the polymeric material permanently or for an extended period, until after the polymeric material has degraded and removed from the site.

In the broadest sense, the bioactive materials can include proteins (as defined herein, including peptides unless otherwise specified), saccharides, polysaccharides and carbohydrates, nucleic acids, lipids, gangliosides, and synthetic organic and inorganic materials.

Specific materials include antibiotics, antivirals, antiinflammatories, both steroidal and non-steroidal, antineoplastics, anti-spasmodics including channel blockers, modulators of cell-extracellular matrix interactions including cell growth inhibitors and anti-adhesion molecules, enzymes and enzyme inhibitors, anticoagulants and/or anti-thrombotic agents, growth factors, DNA, RNA, inhibitors of DNA, RNA or protein synthesis, compounds modulating cell migration, proliferation and/or growth, vasodilating agents, and other drugs commonly used for the treatment of injury to tissue. Specific examples of these compounds include angiotensin converting enzyme inhibitors, prostacyclin, heparin, salicylates, nitrates, calcium channel blocking drugs, streptokinase, urokinase, tissue plasminogen activator (TPA) and anisoylated plasminogen activator (TPA) and anisoylated plasminogen-streptokinase activator complex (APSAC), colchicine and alkylating agents, and aptomers. Specific examples of modulators of cell interactions include interleukins, platelet derived growth factor, acidic and basic fibroblast growth factor (FGF), transformation growth factor β (TGF β), epidermal growth factor (EGF), insulin-like growth factor, and antibodies thereto. Specific examples of nucleic acids include antisense and ribozymes. Specific examples of other bioactive agents include modified extracellular matrix components or their receptors, and lipid and cholesterol sequestrants.

In a preferred embodiment, the bioactive materials are selected to provide chemotactic activity, haptotactic activity, or contact guidance for cells. Chemotaxis is defined as directed migration in response to a concentration gradient of a soluble attractant, i.e., in the gel. A definition is provided in "The Molecular and Cellular Biology of Wound Repair" ed. R. A. F. Clark and P. M. Henson ed., (Plenum Press, NY 1988) Chapter 13. J. B. McCarthy, Sas, and Furcht, the teachings of which are incorporated in. Haptotaxis is defined as the directed migration along an adhesion gradient. Information comes from the substratum; as described herein, by incorporation into the polymeric material of molecules that direct the behavior of the cells. Examples include extracellular matrix proteins such as laminin, fibronectin, vitronectin or collagen, or peptides derived therefrom or having an effect on binding to the proteins, such as the RGD peptides described in the following examples. Contact guidance refers to the physical direction of cells, through grooves, fissures, or pores of the polymeric material, or by incorporation within the polymeric material of particles, ribbons, or fibers which direct cell growth. An example is regeneration of nerve fibers, which does not occur in the absence of physical guidance, as in the form of a sheath.

In applications where multiple polymer layers are used, different pharmacological agents can be employed in different polymer layers to achieve specific effects.

Optional additions to the polymeric material such as barium, iodine or tantalum salts for X-ray radio-opacity allow visualization and monitoring of the coating.

Cells can also be incorporated into the polymeric solution as a suspension which forms a gel at the tissue surface that allows the cells to grow and in some cases to proliferate. The cells can be living (whether naturally occurring or produced through recombinant DNA technology), artificial cells, cell ghosts (i.e., RBC or platelet ghosts), or pseudovirions, to serve any of several purposes. For example, the cells may be selected to produce specific agents such as growth factors at the local tissue location.

Cells incorporated in the material may also be progenitor cells corresponding to the type of tissue at the treatment location or other cells providing therapeutic advantages. For example, liver cells might be incorporated into the polymeric material and implanted in a lumen created in the liver of a patient to facilitate regeneration and closure of that lumen. This might be an appropriate therapy in cases where diseases (e.g. cirrhosis, fibrosis, cystic disease or malignancy) results in non-functional tissue, scar formation or tissue replacement with cancerous cells. Similar methods may be applied to other organs as well.

2. Physical Incorporation of Bioactive Agents.

In most cases, it is possible to physically incorporate the bioactive agent by mixing with the material prior to application to the tissue surface and polymerization. The material can be mixed into the monomer solution to form a solution, suspension or dispersion. In one embodiment, the bioactive agent can be encapsulated within delivery devices such as microspheres, microcapsules, liposomes, cell ghosts or pseudovirions, which in themselves effect release rates and uptake by cells such as phagocytic cells.

3. Chemical Incorporation of Bioactive Agents.

Bioactive agents can be chemically coupled to the polymeric material, before or at the time of polymerization. In the preferred embodiment, the bioactive agents are chemically coupled prior to administration of the polymeric material to the tissue surface. Several polymeric biocompatible materials are amenable to surface modification in which surface bound bioactive molecules/ligands exhibit cellular binding properties. These methods are described by Tay, Merrill, Salzman and Lindon in *Biomaterials* 10, 11–15 (1989), the teachings of which are incorporated herein by reference.

Covalent linkages can be formed by reacting the anhydride or acid halide form of an N-protected amino acid, poly(amino acid) (two to ten amino acids), peptide (greater than 10 to 100 amino acids), or protein with a hydroxyl, thiol, or amine group on a polymer. The amine groups on the amino acid or peptide must be protected before forming the acid halide or anhydride, to prevent self-condensation. N-protection is well known by those skilled in the art, and can be accomplished by use of various protecting groups, such as a carbobenzoxy (CBZ) group.

The term "protecting group" as used herein refers to a moiety which blocks a functional group from reaction, and which is cleavable when there is no longer a need to protect the functional group. Examples of functional groups include, but are not limited to, amino, hydroxy, thio, and carboxylate groups. Examples of protecting groups are well known to those skilled in the art.

A carboxylate-containing compound can contain various functional groups, such as hydroxy, thio, and amino groups, that can react with an acid halide or anhydride. These functional groups must be protected before forming an acid chloride or anhydride to avoid self-condensation. After formation of the acid chloride or anhydride, and subsequent reaction with the hydroxyl, thiol, or amino group(s) on another molecule, the protecting group can be removed in a "deprotecting" step. The N-protected amino groups can be deprotected by means known to those skilled in the art. Any hydroxy or thio groups on these compounds must be protected so as not to react with the acid halides or anhydrides. Examples of suitable protecting groups for alcohols include but are not limited to trialkyl silyl groups, benzyl ethers, and tetrahydropyranyl ethers. These groups can be protected by means known to those skilled in the art, and can be subsequently deprotected after the esterification is complete. Examples of protecting groups can be found in Greene, T. W., and Wuts., P; G. M., "Protective Groups in organic Synthesis, 2d Ed., John Wiley & Sons, Inc., pp. 317–318 (1991), hereby incorporated by reference.

A non-limiting method for preparation of acid halide derivatives is to react the carboxylic acid with thionyl chloride, preferably in benzene or toluene with a catalytic amount of DMF. A known method for producing anhydrides is to react the carboxylic acid with acetic anhydride. In this reaction, as acetic acid is formed, it is distilled out of the reaction vessel. Peptides can be covalently bound to the polymeric material, for example, when the polymeric material is a polymer of an alpha hydroxy acid such as poly(lactic acid), by protecting the amine functionality on the peptide, forming an acid halide or anhydride of the acid portion of the polymer, reacting the acid halide or anhydride with free hydroxy, thiol, or amine groups on the polymer, then deprotecting the amine groups on the peptide to yield polymer having peptide bound thereto via esterification, thioesterification, or amidation. The peptide can also be bound to the polymer via a free amine using reductive amination with a dialdehyde such as glutaraldehyde.

The ester groups on a polyester surface can be hydrolyzed to give active hydroxy and carboxyl groups. These groups can be used to couple bioactive molecules. Preferably, before converting the active carboxylate group to the acid halide or anhydride form, the active hydroxy group is protected to avoid reaction with the resulting acid halide or anhydride. As a non-limiting example, the active hydroxy group can be protected as a benzyl ether. The active carboxyl group can then be converted to the acid halide or anhydride, and reacted with a hydroxy or amino group on a second compound to form an ester or amide linkage. The O-protected hydroxy group can then be deprotected.

Polyanhydrides can be partially hydrolyzed to provide carboxyl groups. The resulting carboxyl groups can be converted to acid halides, which can be reacted with amino acids, peptides, or other amine containing compounds with binding properties and form an amide linkage.

Polyesters and polylactones can be partially hydrolyzed to free hydroxyl and carboxyl groups. The hydroxyl groups can be protected by means known to those skilled in the art, and the carboxyl groups converted to acid halides. The acid halides can be reacted with amino acids, peptides, or other amine containing compounds with binding properties and form an amide linkage.

Alternatively, if the hydroxyl groups are primary or secondary hydroxyl groups, they can be oxidized to aldehydes or ketones, and reacted with amines via reductive amination to form a covalent linkage.

Polyamides can be partially hydrolyzed to provide free amine and carboxylic acid groups. The amine group can then be reacted with an amino acid or peptide in which the amine groups have been protected, and the carboxyl groups have been converted to acid halides. Alternatively, the amine groups on the polyamide can be protected, and the carboxyl groups converted to acid halides. The resulting acid halides can then be reacted directly with the amine groups on amino acids or peptides.

Polyalcohols with terminal hydroxy groups can be appended with amino acids or peptides. One first protects the amine groups, then converts the carboxyl groups on the amino acid or peptide to acid halides. The acid halide can be reacted directly with the hydroxy group to provide an ester linkage.

The acid halides described above can also be reacted with thiol groups to form thioesters.

Application of the Polymeric Materials

1. Administration of Polymeric Material to Tissue Surfaces.

In general terms, the polymeric material is a biocompatible polymeric material having a variable degree of fluency in response to a stimulus, as described above. The material is such that it is substantially non-fluent in vivo upon completion of the coating process. The material, in its fluent form, is positioned in contact with a tissue or cellular surface to be coated and then stimulated to render it non-fluent, as described above. The fluent phase of the polymeric material is applied using catheters, syringes, or sprays, depending on the tissue lumen surface to which it is applied. Such devices are known to those skilled in the art.

The coating typically will be applied using some type of catheter, such as a modified PTCA catheter. The material is preferably applied using a single catheter with single or multiple balloons and lumens. The catheter should be of relatively low cross-sectional area. A long thin tubular catheter manipulated using fluoroscopic guidance is preferred for providing access to the interior of organ or vascular areas.

The tissues involved may be those organs or structures having hollow or tubular geometry, in which case the polymeric products are deposited within the naturally occurring lumen. Alternatively, the tissue may be a normally solid organ in which a cavity has been created either as a result of a surgical procedure, a percutaneous intervention, an accidental trauma, or disease. Examples of hollow vessels include the aorta, coronary arteries, veins and lymphatic vessels. Examples of hollow organs include the heart, the eye, intestine, fallopian tube, uterus, kidney or the bladder. In addition many organs have component structures which are hollow such as the trachea (lung), the biliary duct (gall bladder), or the pancreatic duct (pancreas). In addition to organs around hollow geometries many solid organs possess internal "true" spaces, such as cavities, cavernous sinuses or lumens, or "potential" spaces, following a disease process which creates the space, i.e., the interior of a necrotic tumor.

Once the fluid phase of the polymeric material has been applied, the fluid state of the material is reconfigured to form a coating or "paving" layer in intimate and conforming contact with the surface. The resulting paving layer can have a sealing function, i.e., it forms a coating of sufficiently low porosity that it excludes macromolecules (i.e., less than 53 Angstroms for a protein up to 2000 Angstroms for a rod such as myosin) and cells (600 nm for platelets up to 30 to 40 microns for large cells). The coating preferably has a thickness on the tissue surface on the order of 0.001–1.0 mm, however, coatings having a thickness outside this range may be used as well. By appropriate selection of the material employed, using materials commercially available, and methods for crosslinking that are known to yield a specific percent crosslinking and porosity, and of the configuration of the paving material, the process can be tailored to satisfy a wide variety of biological or clinical situations.

The polymeric materials may be applied in custom designs, with varying thicknesses, lengths, and three-dimensional geometries (e.g. spot, stellate, linear, cylindrical, arcuate, spiral) to achieve varying finished geometries. Further, the process may be used to apply material to the inner surfaces of hollow, cavernous, or tubular biological structures (whether natural or artificially formed) in either single or multi-layer configurations. The process may also be used, where appropriate, to occlude a tissue lumen completely.

2. Application of Polymeric Material to Isolated Cells and Cell Aggregates.

The polymeric material may also be applied to cellular surfaces, for example to coat or encapsulate individual or multiple cells such as blood components, smooth muscle cells, endothelial cells and tumor cells that are being removed and are treated to prevent attachment if accidently detached and left in the patient. In general, this methodology would be used to isolate the treated cells.

In a second embodiment, the polymeric material is used to protect and attach isolated cells or cell aggregates to an area within the body where it cell attachment, growth and/or proliferation is desirable. One process involves first inserting a catheter into a lumen within a diseased organ segment. The lumen can be a native vessel or it can be a man-made lumen. A polymeric plug is introduced into the lumen. The catheter is then removed, leaving the plug in place to act as a focus for new growth stemming from cells implanted along with the polymeric plug. If the desire is for a more tubular structure, the plug can be appropriately reconfigured.

3. Representative Devices for Application of Polymeric Material.

FIG. 1 is a schematic of the process for applying polymeric material to a tissue lumen. In step 1, a lesion in the lumen is identified and isolated. In step 2, a catheter, optionally a balloon catheter consisting of a tubular shaft which includes one or more balloons, is inserted into the lumen. In the preferred embodiment for the treatment of blood vessels, the distal occlusion balloon is used to occlude the distal end of a treatment site. In embodiments where the lumen can be rinsed clean, for example at an end artery or in the gastrointestinal tract or lungs, it is not necessary to inflate the balloon. In any case, the treatment site is cleared of blood, mucous, or other extraneous material, as shown in step 3. The site may then be treated with drugs, for example a drug inhibiting responsiveness to mechanical stimuli or cell proliferation, as shown in step 4. In step 5, if appropriate, the lesion itself is treated by expansion of the balloon, in the case of an arterial plaque, or by other mechanical, thermal, optical, photochemical, ultrasonic, or radiation means. As shown in step 6, the site is again treated with drugs and/or washed or compounds to increase adhesiveness applied. In step 7, the solution for forming the polymeric material at the tissue surface is applied and polymerized or solidified. In some embodiments the catheter includes a "mold core" which is used to shape the polymeric material so that it covers only the area to be treated in a thin layer. The central mold core member may be able to adjust size, i.e., for a balloon it may be underinflated to not occupy the maximum space, thereby leaving room for the polymeric material. The polymeric material may be shaped as a uniform layer, or patterned or segmented as desired. In step 8, the catheter is removed and flow of material through the polymeric coated lumen restored.

Two other embodiments of delivery catheters that can be utilized for application of the polymeric material are shown in FIGS. 2A, 2B and 2C. FIG. 2A is a single entity with means for entering a tissue lumen, isolating a zone, washing, applying a drug, adhesive and/or a polymeric material and a core forming member and/or dilating member. The catheter 11 is constructed with two isolation balloons 10, 14, and a central dilating or molding balloon 12, as well as a plurality of lumens and an attached reservoir 16 for delivering washing fluid, drug, adhesive and/or polymer. A detailed cross-section enlargement of the tip of the application device is shown in FIG. 2A. Two isolation balloons 18, 22 are constructed out of elastomeric material, i.e., latex, krayton or C-flex or thermoplastic polymers such as polyethylene, polyolefin co-polymer, polyethylene terepthalate, or nylon. The balloons 18, 22 are attached to a multilumen shaft 43 including a central lumen 42 running the length of the device to allow flushing or passage over a guide wire (not shown). A central mold-core balloon 20 is fabricated out of similar materials to those forming the isolation balloons 18, 22, or from less compliant materials so that it opens to a designated dimensions without a continuous stretch or expansion via creep of the balloon material. In addition, lumens exist for filling the isolation balloon 24, 26 and for instilling, filling or removing fluid from the dilating or mold core balloons 32, 34. In addition, there are lumens 30, 36 for instilling fluid into the isolation zone. Lumens 38, 40 are used to instill fluid or remove fluid from the isolation zone. This device provides a means to instill, perfuse, or superfuse a zone.

FIG. 2C shows another catheter 45 encompassing two telescoping members 46 within 44. Zone isolation balloons 50 and 52 and a central mold core and/or dilating balloon 54, as well as instillation or aspiration ports 56, provide an alternative means for applying polymeric material.

The material may also be applied to the surface to be coated by spraying, extruding or otherwise internally delivering the material in a fluent form via a delivery device having single or multiple lumens.

Application of the coating material may be accomplished by extruding a solution, dispersion, or suspension of monomers, polymers, macromers, or combinations thereof through a catheter to coat or fill a tissue or cellular surface, a tissue lumen or a hollow space. The formation of the coating can be controlled by introducing crosslinking agents, gelling agents or crosslinking catalysts together with the fluent material and then altering the conditions such that crosslinking and/or gelling occurs. Thus, when a balloon catheter is used, a flow of heated or chilled fluid into the balloon can alter the local temperature to a level at which gelling or cross-linking of introduced material is induced, thereby rendering the material non-fluent. Localized heating or cooling can be enhanced by providing a flow of heated or chilled liquid directly onto the treatment site. Thermal control can also be provided, however, using a fluid flow through or into the balloon, or using a partially perforated balloon such that temperature control fluid passes through the balloon into the lumen. Thermal control can also be provided using electrical resistance heating via a wire running along the length of the catheter body in contact with resistive heating elements. This type of heating element can make use of DC or radio frequency (RF) current or external RF or microwave radiation. Other methods of achieving temperature control can also be used, including light-induced heating using an internal optical fiber (naked or lensed). Similar devices can be used for application of light, ultrasound, or irradiation.

Catheter bodies are made of standard materials, including metals such as surgical steel and thermoplastic polymers. Occluding balloons may be made from compliant materials such as latex or silicone, or non-compliant materials such as polyethylene terephthalate (PET). The expansible member is preferably made from non-compliant materials such as PET, (PVC), polyethylene or nylon. If used, the balloon portion of a dilatation catheter may optionally be coated with materials such as silicones, polytetrafluoroethylene (PTFE), hydrophilic materials like hydrated hydrogels and other lubricous materials to aid in separation of the polymer coating.

Medical Indications for Treatment

1. Treatment of Lumen Surfaces

In addition to treatment of arteries, the method described herein can be utilized for other applications such as paving the interior of veins, ureters, urethras, bronchi, biliary and pancreatic duct systems, the gut, nasolacrimal ducts, sinus cavities, the eye, and eustachian, spermatic and fallopian tubes. The process can be used to provide a paving layer in the context of transjugular intrahepatic portosystemic shunting procedure (TIPS), dialysis grafts, arterio-venous fistulae, and aortic and other arterial aneurysms, as well as in the treatment of abrupt vessel reclosure post PCTA, the "patching" of significant vessel dissection, the sealing of vessel wall "flaps" either secondary to catheter injury or spontaneously occurring, and the sealing of aneurysmal coronary dilations associated with various arteritidies.

The ultimate in vivo geometry of the material dictates the final function of the coating. The thinner applications allow the polymer film to function as a coating, sealant, partitioning barrier, bandage, and/or drug depot.

The hollow or cavernous geometry present in many body components has functional significance. Such geometry facilitates fluid (blood, urine, lymph, bile) gas, a cellular (ovary, spleen) containment or transport. These hollow vessels, organs and organ components are typically composed of several tissue layers. Generically these organs are composed of an inner cellular layer typically functioning as a barrier layer, one or several middle functional layers containing muscularis, glands or other functional tissue, and an external supportive or stromal covering layer.

Disease may effect the innermost layer of these hollow organs and thereby violate their barrier function. Diseases can be either: (1) systemic with overall diffuse constitutional manifestations, (2) systemic with localized specific intra-organ focal involvement, or (3) localized only with definitive regional intra-organ involvement. Examples of such diseases include spontaneous plaque rupture, unstable angina, non-cardiogenic pulmonary edema, sepsis, and erosive/infiltrative tumors.

2. Manipulation of Cell-Cell Interactions

The methods described herein restore the barrier function, and/or provided controlled drug delivery, thereby providing a method for treatment for these disorders. The polymeric material can also served as a trophic layer, an adhesive layer, as a coating of other therapeutic intraluminal devices, as an absorbing layer, as a sequestrant, or chelator.

As described above, in a particularly preferred embodiment, the polymeric material is used to apply an effective amount of bioactive molecules such as chemotactic molecules, haptotactic molecules or molecules providing contact guidance, to a site where the bioactive molecules would otherwise not reach in an effective dosage. In the case of cell to cell interactions, the polymeric materials provide a substrate that is analogous to the cell surfaces on which these molecules are normally found and therefore appear to be significantly more effective than administered in the same dosage in the absence of the polymeric material.

Materials such as attachment peptides, selectin receptors and carbohydrate molecules such as Sialyl $Le^x$, can be used which serve to attract and bind specific cell types, such as white cells and platelets. Materials such as fibronectin, vimentin, and collagen, can be used to non-specifically bind cell types, to facilitate cell migration and thereby to enhance healing. Growth factors and modulators of cell growth, proliferation and migration are particularly useful.

For example, one may incorporate into the polymeric material a chemoattractant factor to cells such as PDGF or matrix proteins, i.e., fibronectin, laminin, fibrin, or type IV collagen, which will then facilitate cell ingrowth for wound repair or a gap or rent resulting from disease. In a preferred example for endothelial cells, heparin, macrophage chemotactic factor (Varki, Ajit P., et al., *Proc. Natl. Acad. Sci. USA* 78:7773–7777 (1981)), basic FGF or tumor angiogenesis factor can be used to facilitate repair post angioplasty, atherectomy, stenting or vascular surgery. In a preferred example for treatment of bladder cancer following administration of chemotherapeutic agents such as BCG, EGF is applied in a gel to coat the bladder. EGF can be similarly applied in a polymeric gel following cryosotherapy of the cervix to facilitate re-epithelization.

To aid in organ repair, a paste or layer of gel incorporating growth factors can be applied adjacent to injured organs to enhance organ regrowth after disease or surgery. Embryonic cardiomyocytes plus growth factor can be seeded in a polymeric gel in artificial lumens decreased in diseased, for example, myocardium following heart failure or infarction, for cell repopulation and creation of "mini-organs" of contractile function. Thinning with eventual rupture of the septum and the creation of a VSD leads to communication between the ventricles and the acute onset of heart failure with significant associated mortality. Currently, Dacron™ patches are inserted to stabilize blood flow and pressure but they leave a large zone in the septum which is non-functional. Using the polymeric material applied to the composite in combination with bioactive molecules can facilitate repair and regrowth.

Chief cells of the parathyroid can be incorporated into a polymeric gel and locally implanted to form islands of local parathyroid hormone production following parathyroid destruction or removal associated with thyroid removal, which is a particularly significant problem following resulting in altered calcium and phosphate metabolism.

In addition to functional alteration and disease processes in tubular organs many non-tubular organs and tissue surfaces may also undergo a change in either function or structure due to aging, disease or injury. As an example, if a tumor is found on a tissue surface in an internal organ, current therapy involves local surgical excision to create a disease free margin. To prevent further disease progression into the normal zone either external, often toxic, chemotherapy is administered or the patient is subjected to radiation therapy. These therapies result in many side effects and are frequently of limited effectiveness. Using the method described herein, one can locally apply a coating of polymeric material to a tissue surface which alone, or by incorporated anti-proliferative chemotherapeutic agents or bioactive substances limit the ingrowth of tumor cells. One can also utilize bioactive molecules which selectively favor the ingrowth of normal parenchymal cells or the overgrowth of epithelial cells.

The polymeric material is particularly useful as an enhancement to healing following normal surgical procedures where the wound is closed using sutures or staples.

In another example, one can use the method and polymeric compositions described herein in combination with an adhesion receptor antagonist peptide containing the amino acid sequence Agr—Gly—Asp to deliver the peptide (the drug) to a site where abnormal tissue growth via cell migration and proliferation is occurring in a concentration which would effectively inhibit cell-extracellular matrix interactions which promote inappropriate cell attachment and migration within the targeted tissue.

Still another example of the application of this method and polymeric compositions, demonstrated by the following examples, is in the prevention of restenosis of diseased blood vessel after interventional therapy. Local delivery of an RGD-containing peptide via a hydrogel is delivered for a sufficient amount of time to block inappropriate smooth muscle cell migration within the vessel wall which leads to vessel wall thickening and restenosis.

The present invention will be further understood by reference to the following non-limiting examples.

EXAMPLE 1

In vitro application of polymer to a mock hollow organ.

A catheter was inserted into a mock blood vessel constructed from a clear plastic Tygon™ tube. The distal occlusion balloon was expanded to define a treatment site, and Pluronic™ F127 in its fluent form was injected into the vessel through the catheter. A mold core balloon was inflated, and the Pluronic™ gel material was allowed to warm and gel. Finally the balloons were deflated and the catheter was withdrawn, leaving a gel coating on the interior surface of the "vessel" lumen.

As shown in detail in FIGS. 3A–3G, FIG. 3 reveals an actual example of use of the balloon application catheter as outlined in FIG. 2C above for the application of a flowable gel polymer in a thick hollow tubular structure. A telescoping gel paving catheter is shown in FIG. 3A. This catheter consists of a proximal hollow shaft 64 with an end annular occlusing balloon 58 (i.e., the proximal occlusion balloon). Telescoped within the proximal shaft is a second smaller shaft 62 with an attached distal occluding balloon 60 and a mold core or gel paving balloon 66. In FIG. 3B the catheter assembly is placed within the lumen 68 of a mock hollow tubular organ, in this case clear Tygon™ tubing.

In FIG. 3C the proximal and distal occluding balloons are shown inflated, isolating a zone 70 of the hollow tubular organ.

In FIG. 3D, a flowable polymeric solution 72 has been instilled within the isolation zone. In this example Pluronic™ F127 (25% v/v) at 4° C. was utilized with the solution colored with dissolved Toluidine Blue for visibility. In FIG. 3E the polymer has warmed and gelled, thereby gelling the instilled fluid. Note that the proximal and distal occlusion balloons have been deflated yet the colored polymer 74 remains contained within the zone, demonstrating its gelled nature.

In FIG. 3F the application catheter has been removed leaving a gel coating 76 in the zone with a central hollow lumen 78.

In FIG. 3G a thinner coating of the polymer 80 is seen which has been achieved via a second retrograde passing of the distal occlusion balloon 60 through the coated zone further smoothing and forming the gel to yield a thin coating.

EXAMPLE 2

In vitro application of polymer to an isolated blood vessel segment.

A segment of a blood vessel was excised. The catheter was inserted into the interior of the vessel. A chilled Pluronic gel F127 in its fluent form was injected through the catheter into the space between the catheter and the vessel wall, and the mold core balloon was expanded. Once the polymer had warmed to a temperature sufficient to cause gelling, the mold core balloon was deflated and the catheter removed.

Figure 4A:
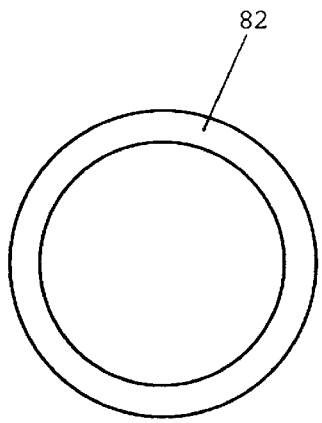
FIGS. 4A–4F are schematics of micrographs of injection of polymeric material into isolated bovine coronary arteries.
Figure 4B:
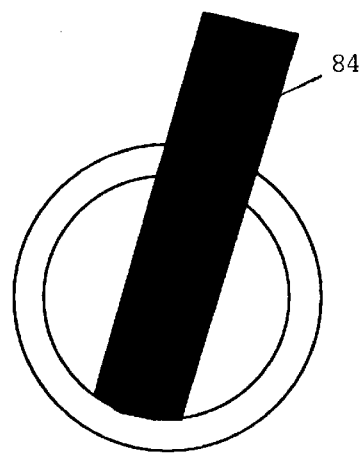
Figure 4C:
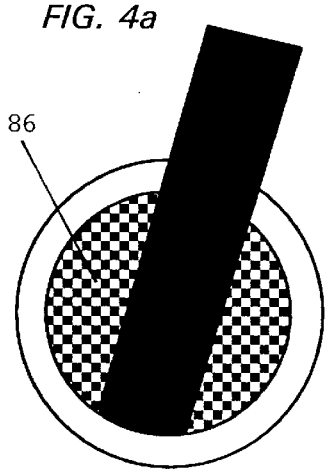
Figure 4D:
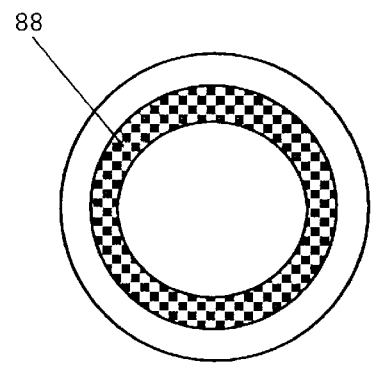
Figure 4E:
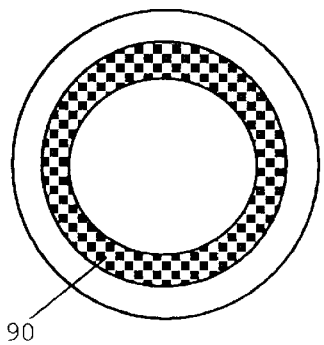
Figure 4F:
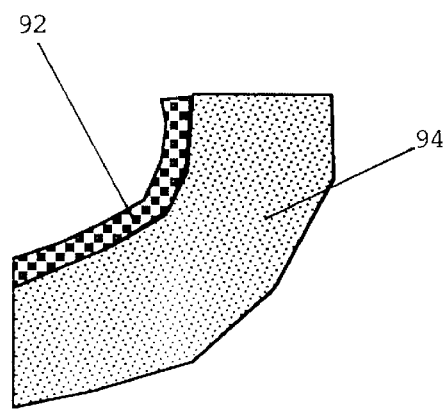

FIGS. 4A–4F are micrographs showing application of a gel coating to isolated bovine coronary arteries using a "mold-core" central catheter. In FIG. 4a a segment of an isolated bovine coronary artery 82 is seen in cross-section. In FIG. 4B a mold core catheter 84 has been placed centrally within the lumen. In FIG. 4C a flowable colored polymeric solution 86 (Pluronic™ F127 25% (w/v) plus Toluidine Blue) has been instilled by injection into the lumen occupying the space defined by the mold core balloon and the endoluminal surface of the vessel. In FIGS. 4D and 4E, upon gelation of the polymer and removal of the catheter, a thin annular coating of polymer gel 88, 90 is seen in intimate contact on the vessel endoluminal surface. In FIG. 4F the gel coated or paved artery is seen under magnification (6×) and a thin endoluminal gel layer 92 is identified which is adherent and conforming to the underlying arterial wall 94.

The resulting tissue surface is paved with a Pluronic™ polymerge gel in a manner which coats the surface and fills and conforms irregularities on the surface. Further, the deployed interior surface of the gel is smooth, thereby providing a barrier layer having a Theologically advantageous surface with improved blood flow.

Figure 5:
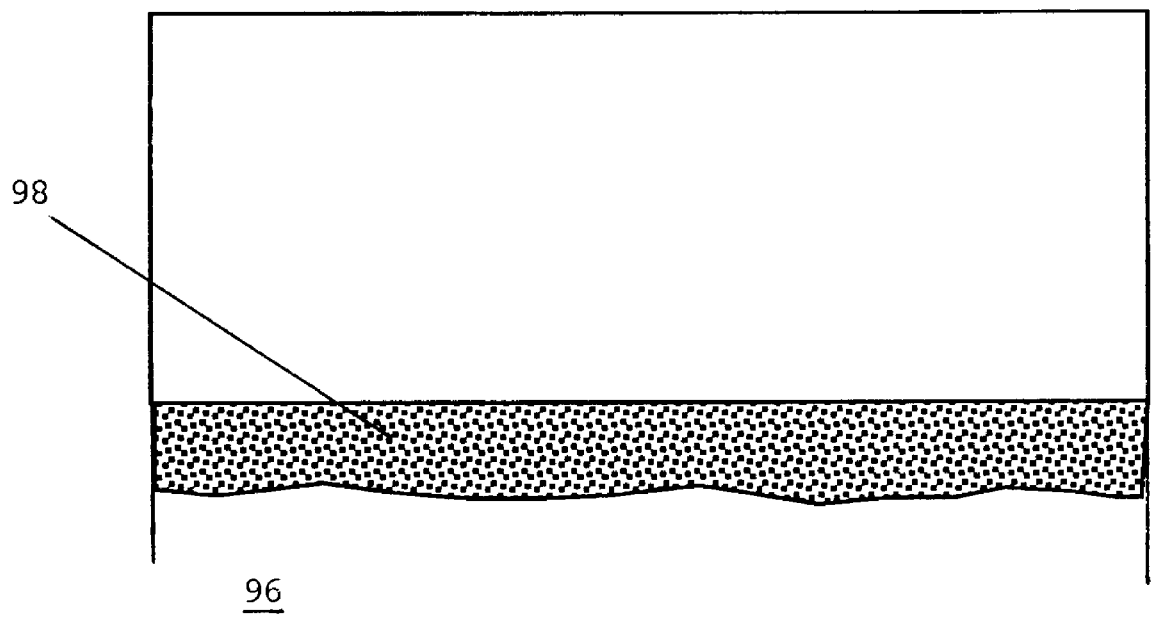
FIG. 5 is a schematic of micrograph (250×) of the cross-section of a gel coated artery with a thin gel coating (lower left corner).

FIG. 5 is a micrograph of a frozen cross-section (250×) of a gel coated bovine coronary artery. A thin layer of gel 96, formed as described above, is seen in intimate conformal contact with the underlying endoluminal (intimal) surface 98 of the vessel.

EXAMPLE 3

Thermoreversible polyether hydrogels reduce the thrombogenicity of injured arterial intimal surfaces in vitro and ex vivo.

Polymeric Endoluminal Paving is a generic method of applying thin layers of biodegradable polymers to the endoluminal surface of hollow body structures. The applied polymer layers may function as temporary wall supports, barriers or localized sustained drug delivery vehicles. Studies to date utilizing structural polyesters in the vasculature have demonstrated that endoluminal paving layers may be effectively applied in situ via localized catheter-based thermoforming, being structurally stable, wall-supportive and hemocompatible.

As an extension of the paving method recent studies have examined the feasibility of applying a layer of non-structural polymeric hydrogels to arterial endoluminal surfaces to act as a short term barrier, locally reducing injured arterial surface thrombogenicity. Studies using biodegradable and erodible polyethers (PE) were conducted to determine the blood compatibility of PE gels in vitro, the ability of PE gels to reduce the thrombogenicity of acutely injured arterial surfaces in vitro, and the ability of endoluminal PE gels to thromboprotect injured arterial surfaces ex vivo.

Materials and Methods

Spin-cast gel films of PE on glass, and strips of intima-abraded freshly explanted rat aorta (ex vivo) (Ao) on which PE gels were formed, were placed in a parallel plate flow chamber and exposed to overflowing heparinized (2 U/ml) mepacrine-labeled (10 mM) fresh human blood (100 $sec^{-1}$ shear rate, 37° C.). Surfaces were examined after 5 min. using epifluorescence videomicroscopy and the number of adherent platelets (pl), aggregates of 3–10 pl (pa) and thrombi (t) per 1000× field were measured. Films of Gelatin on glass and non-coated abraded rat aorta served as controls.

Results

| Surface | n | pl/field | pa/field | t/field |
|---|---|---|---|---|
| Gelatin (reference) | 3 | 132.8 ± 38.8 | 12.8 ± 3.1 | 6.8 ± 2.9 |
| PE gel on glass | 3 | 1.40 ± 0.4* | 0* | 0* |
| Abraded Ao (control) | 4 | 204.8 ± 44˙ | 23.8 ± 6.3 | 6.5 ± 1.0 |
| Abraded Ao 4 PE gel | 6 | 1.6 ± 0.5* | 0* | 0* |

*($p < 0.05$)

Similar results were obtained with other polymeric materials including neutralized poly(acrylic acid), pH 7.4 (Carbopol™ 934 and 940, B.F. Goodrich).

EXAMPLE 4

Thermoreversible polyether hydrogels reduce the thrombogenicity of injured arterial intimal surfaces and subsequently limit the eventual development of neointimal hyperplasia in vivo.

Acute thrombosis of injured arterial intimal surfaces is a potentially serious complication following angioplasty, thrombolytic therapy and stent placement. A study was conducted to determine whether formation of thermoreversible polyether hydrogels directly on injured arterial subintimal surfaces would limit subsequent platelet deposition and thrombus formation in vivo.

Materials and Methods

Bilateral carotids in five rats were exposed, segments of paired arteries isolated via atraumatic clips, washed free of blood with normal saline and balloon abraded (2fr Fogarty× 3). In one carotid per animal, chosen to be the control vessel, blood flow was then restored. In the corresponding experimental carotid a layer of polyether hydrogel was then applied to the endoluminal surface following which blood flow was restored. Note: In the experimental vessel care was taken to prevent injured surface re-exposure to blood until after the polymer was applied. Following one hour of blood re-flow, animals were heparinized (200 U/kg), sacrificed via anesthesia overdose, bilateral carotids washed with saline and pressure fixed (90 mm Hg, 2% glutaraldehyde) in situ. Vessels were then excised, examined grossly, and via stereomicroscopy and scanning electron microscopy.

Results

| Group | n | Platelets/hpf (3000x) |
|---|---|---|
| Abraded (Control) | 5 | 90 ± 8 |
| Abraded + PE gel | 5 | *5 ± 9 |

*($p < 0.05$)

Figure 6A:
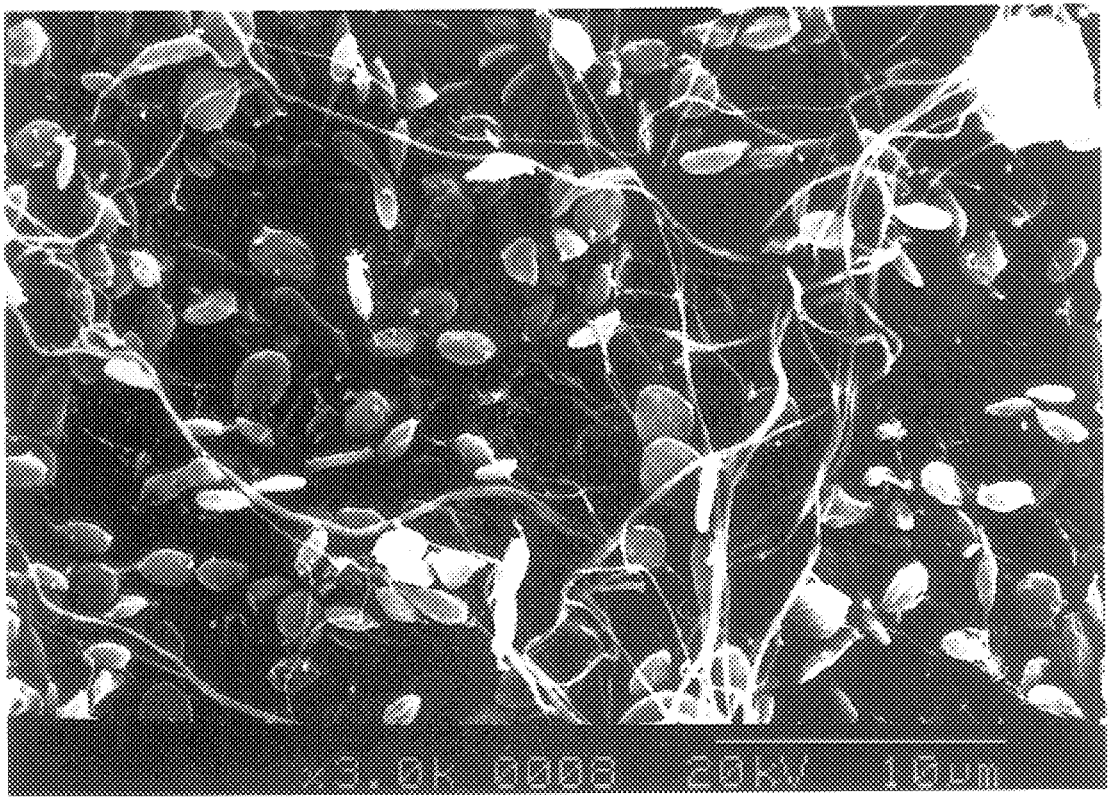
FIGS. 6A and 6B are scanning electron micrographs of the intimal surface of rat carotid arteries following 60 minutes of reexposure to blood post-injury.
Figure 6B:
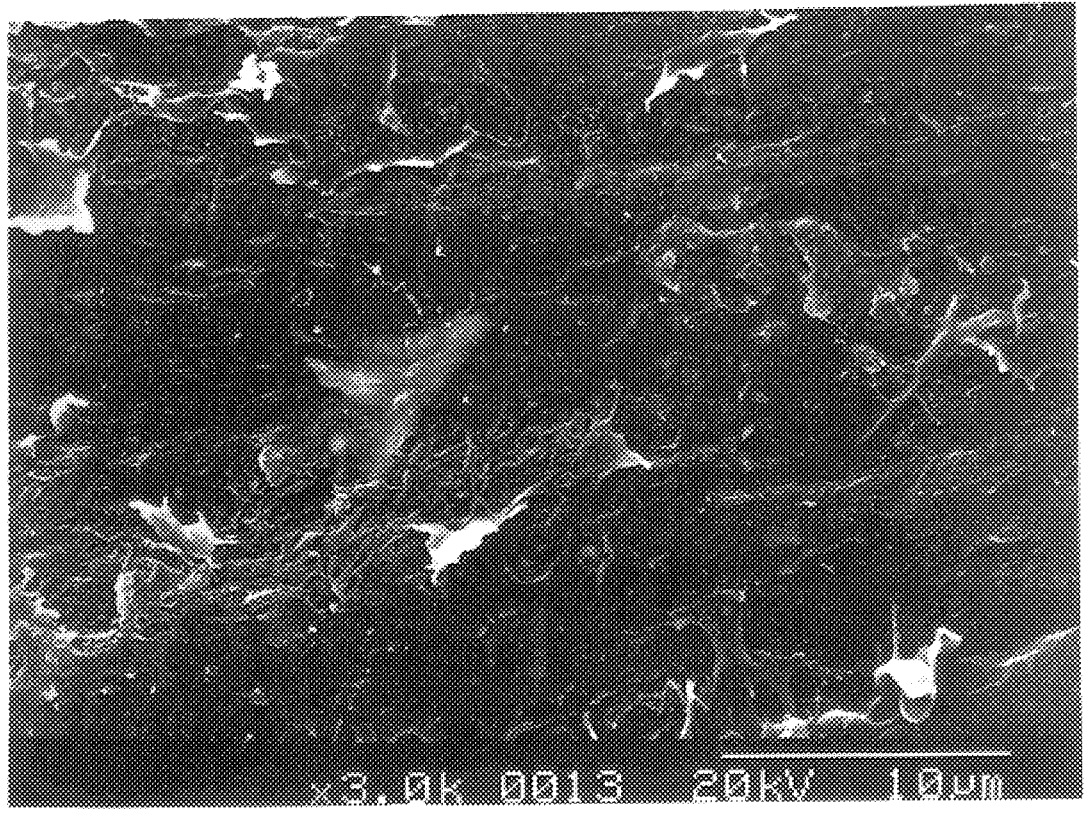

The results shown in FIGS. 6A (control) and 6B, demonstrate that there is almost no deposition of platelets, white cells and fibrin on the treated vessel, in contrast to the untreated control.

The analysis showed that 7±1 thrombi were detected on control aortas. No thrombi were seen on gel coated injured arterial surfaces. 205±44 single platelets were detected on the control surfaces versus 2±1 platelets on the coated artery. ($p<0.05$)

Figure 7A:
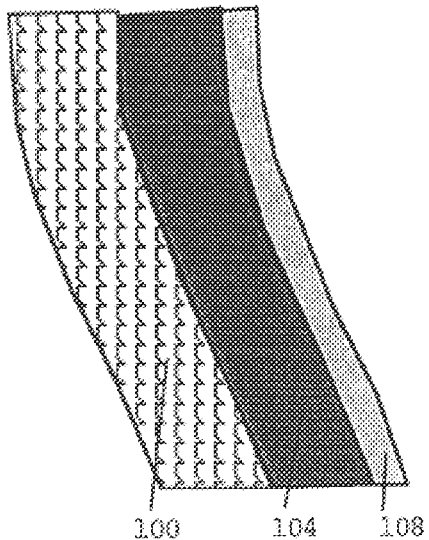
FIGS. 7A and 7B are schematics of photographs of the effect of gel coating on limiting the development of arterial neointimal hyperplasia 14 days post-injury.
Figure 7B:
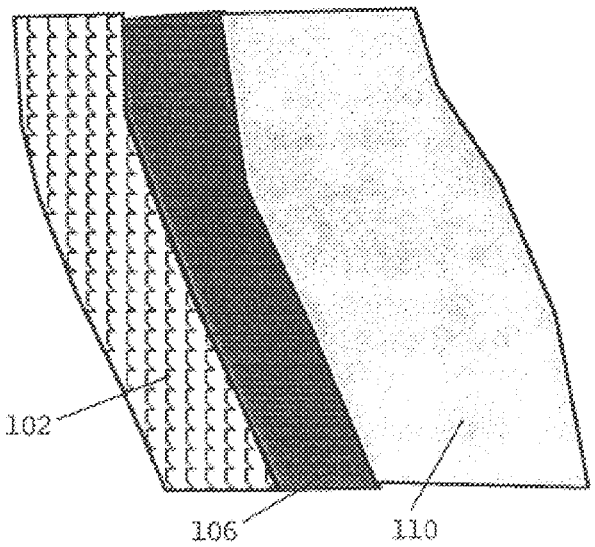

FIGS. 7A and 7B are representative examples of histologic cross-sections of rat carotid arteries harvested 14 days post balloon abrasion injury. The artery 102 in FIG. 7B is an example of a control artery that had been balloon abraded and allowed to heal for fourteen days, without receipt of a gel coating following injury. There is significant neointimal thickening 110 with an almost doubling in thickness compared with the underlying media 106.

In comparison, the gel treated artery 100 in FIG. 7A has a significant reduction in neointima 108. This artery was coated with Pluronic™ F127 (25% w/v) gel and then re-exposed to overflowing blood and allowed to heal for fourteen days.

Conclusions

Polyether gels are hemocompatible and provide a surface which is minimally platelet activating. Thermoreversible polyether hydrogel layers formed directly on injured arterial surfaces, either in vitro or in vivo, create an effective physical barrier layer limiting platelet deposition and thrombus formation with an overall reduction in intimal surface thrombogenicity.

EXAMPLE 5

Delivery of adhesion receptor ligands or other adhesion receptor modulators to a selected local site in vivo as a treatment of disease.

Background

During the past two decades, the base knowledge of cell adhesion and migration in extracellular matrices (ECMs) at the molecular level has expanded rapidly. Early efforts in this area of research concentrated on the adhesion-promoting ECM protein fibronectin (FN). Studies which employed limited proteolysis of FN revealed a 120 KD polypeptide fragment of FN which supported cell adhesion in a way similar to the whole molecule. This fragment existed as a domain embedded in the FN molecule and was designated the cell-binding domain. Further sequence analyses and peptide mapping of the FN cell-binding domain yielded a minimal sequence which maintained cell-binding activity in the tetrapeptide Arg—Gly—Asp—Ser (RGDS).

The biological interaction of the RGDS sequence with cell-surface fibronectin receptors was revealed by demonstrating that synthetic RGDS-containing peptides in solution could competitively inhibit fibroblast cell spreading on fibronectin-coated substrates. Soluble RGDS also inhibited the direct binding of radiolabeled fibronectin to fibroblastic cells in suspension. These competition studies indicated that the RGD sequence is critical for the cell adhesive function of the parent molecule.

After the RGD cell adhesion recognition site in fibronectin was identified, the sequences of other cell adhesion proteins were examined for related signals. Other proteins known to carry functional RGD sequences include the platelet adhesion proteins fibrinogen and von Willebrand factor, osteopontin, and laminin. These findings imply that RGD is a ubiquitous cell adhesion signal.

Isolation of RGD-directed cell-surface receptors for various cell adhesion proteins from many cell types was performed using affinity chromatography on Sepharose carrying the appropriate, covalently bound, adhesion protein. Cell-surface adhesion receptors from cell extracts were observed to specifically bind to these columns and were eluted with RGD-containing peptide solutions. The use of fibronectin as the affinity ligand yielded a receptor that was a heterodimer with a 160 kD α-subunit and a 140 kD β-subunit. Similar affinity chromatography experiments have yielded distinct heterodimeric RGD-directed receptors specific for vitronectin and a platelet receptor with affinities for fibrinogen and fibronectin. It was realized that the heterodimeric structure was characteristic of RGD-directed receptors, with α-subunits ranging between 140 and 160 kD and β-subunits ranging between 90 and 140 kD. These RGD receptors, known as integrins, form the integrin superfamily of cell-surface adhesion proteins.

The integrin superfamily is an important and well characterized group of cell-surface receptors for both cell-substrate and cell—cell adhesion. Integrins are characteristically membrane-spanning heterodimeric protein complexes consisting of an α-subunit and a β-subunit. Fourteen distinct α-subunits and 11 β-subunits have currently been isolated and identified, and several αβ combinations have been observed. Integrin complexes containing $\beta_1$ and $\beta_3$ submits generally are involved in cell adhesion to the extracellular matrix, while the $\beta_2$ integrins are involved in cell—cell adhesion.

Integrins typically bind to cell adhesion proteins via the rather highly conserved sequence Arg—Gly—Asp X (RGDX), where X is variant depending on the particular cell adhesion protein. It was observed that by varying this flanking residue, the affinity of the RGDX ligand for particular integrins was modified, but selectivity for specific integrins was not achieved. Further studies indicated that cyclization of RGDX-containing peptides created a ligand which was highly selective for integrin $\alpha v \beta_3$, the vitronectin receptor. Other studies confirmed that RGD sequences that are conformationally constrained within cyclic peptides bound with higher affinity and selectivity for integrin $\alpha v \beta_3$ than linear RGD sequences. Extracellular administration of cyclic RGD peptides has been shown to inhibit cell adhesion and migration on vitronectin-coated substrates in vitro.

The cyclic RGD peptide class of adhesion ligands is a good example of a class of compounds which could be utilized for the treatment of diseases where cell proliferation and migration in the affected tissues occurs. While cyclic RGD peptides have been shown to selectively inhibit specific cell-ECM interactions, they must reach their preselected and specific target tissues in order to be therapeutically effective. Systematic administration of cyclic RGD would typically be an unsatisfactory therapeutic strategy since significant interference with normal cell-ECM interactions as well as those of targeted cells would occur. The quantity of peptide would could effectively be delivered would also be enormous. A more appropriate therapy would be to deliver cyclic RGD locally to the targeted site.

A specific therapeutic strategy which would greatly benefit from an adjuvant treatment to prevent cell migration is percutaneous transluminal coronary angioplasty (PTCA, balloon angioplasty). Intimal hyperplasia or thickening of the vascular wall, a fundamental mechanism of restenosis, is caused by accelerated growth and wall matrix protein secretion of smooth muscle cells (SMCs) within the vessel wall followed by SMC migration from inside the vessel wall to the luminal or internal blood-contacting surface of the vessel wall. This SMC response to injury is marked by a transformation of SMC phenotype from a quiescent, contractile state to a synthetic, proliferative state in a high percentage of the medial SMCs. Another important event which occurs following injury is that SMCs (both synthetic and contractile SMCs) become migratory moving from the media to the intima.

A recent in vitro study examined the role of $\beta_1$ and $v\beta_3$ integrin receptors in promoting SMC adhesion and migration on substrates coated with fibronectin (FN), laminin (LN), vitronectin (VN), type I collagen (I), and type IV collagen (IV). Using functionally blocking antibodies directed against specific integrin complexes, they found that SMC adhesion on the FN-, LN-, VN-, I-, or IV-coated substrates depended exclusively on functioning $\beta_1$ integrins and that SMC migration on these substrates depended to a large extent on the $\alpha v \beta_3$ integrin (Clyman et al.) Specific peptides are described in U.S. Pat. Nos. 4,517,686 to Ruoslahti, et al., 4,589,881 to Pierschbacher, et al., 5,169, 930 to Ruoslahti, et al., 5,149,780 to Plow, et al., 4,578,079 to Ruoslahti, et al., 5,041,380 to Ruoslahti, et al., and Pierschbacher and Ruoslahti, *J. Biol. Chem.* 262(36), 17294–17298 (1987), Mohri, et al., *Amer. J. Hem.* 37:14–19 (1991), Aumailley, et al., *FEBS* 291(1), 50–54 (1991), Gurrath, et al., *Eur. J. Biochem.* 210, 911–921 (1992), and Scarborough, et al., *J. Biol. Chem.* 268(2), 1066–1073 (1993), the teachings of which are incorporated herein. Ligand affinity chromatography and immunoprecipitation analyses identified a unique series of $\beta_1$ integrins binding to each matrix component: FN ($\alpha_5 \beta_1$, $\alpha_3 \beta_1$, $\alpha v \beta_1$), LN ($\alpha_1 \beta_1$, $\alpha_7 \beta_1$), VN ($\alpha v \beta_1$), I ($\alpha_1 \beta_1$, $\alpha_2 \beta_1$), and IV ($\alpha_1 \beta_1$). The $\beta_3$ integrin, $\alpha v \beta_3$, was observed to bind to all of the adhesion proteins tested (FN, LN, VN, I, and IV). These studies suggested that induction of SMC migration required a switch from an immobile state, consisting of stable $\beta_1$ integrin interactions with the ECM, to a mobile state, where cells form transient interactions with the ECM via integrin $\alpha v \beta_3$. These studies suggested that cyclic RGD should be a potent inhibitor of SMC migration since it could specifically block integrin $\alpha v \beta_3$ interactions with the ECM.

Study demonstrating local delivery of a cyclic RGD Peptide Inhibits Neointimal Hyperplasia Following Balloon Injury.

A study was therefore conducted in order to assess whether one could provide a method of local delivery of cyclic RGD to an injury site in a vessel wall in vivo, i.e. a site where PTCA was performed, so that localized inhibition of intimal SMC migration would occur which could effectively reduce intimal hyperplasia. Specifically, a study was conducted to determined whether interference with integrin-matrix interactions in the arterial wall, through localized delivery of a cyclic integrin antagonist peptide, would alter the degree of neointimal hyperplasia development at 14 days in a rat balloon injury model.

The left carotid artery in 10 rats (male, 350 g) was balloon abraded (2Fr fogarty×3). In five of the ten rats the integrin antagonist cyclic peptide GPenGRGDSPCA (cRGD) was mixed to a concentration of 1 mM Pluronic gel (500 μl) and locally applied to the adventitia of the injured artery. The five untreated rats served as controls.

At 14 days the rats were sacrificed, carotid arteries pressure fixed and mean intima and media thickness determined. The mean intima/media ratio (I/M) of control balloon abraded arteries was 2.09±0.54. The mean intima/media ratio was 0.17±0.10 in the abraded cRGD treated arteries ($p<0.001$).

These results demonstrate that local application of cRGD peptide leads to a 92% reduction in the degree of hyperplasia. There was no significant change in media thickness between the groups. The localized application of an integrin antagonist to the arterial wall following balloon injury modifies the normal healing response resulting in a significant reduction in neointimal hyperplasia development.

EXAMPLE 6

Comparison of the efficacy of locally delivered linear RGD peptide compared with cyclic RGD peptide in limiting post-injury neointimal hyperplasia.

Cell-matrix interactions, mediated via cell surface integrins and extracellular matrix protein ligands, have been shown to regulate cell phenotype and function. As described in the foregoing examples, interference with integrin-matrix interactions in the arterial wall, through localized delivery of a cyclic integrin antagonist peptide, GPenGRGDSPCA (cRGD), resulted in a 92% inhibition in the development of neointimal hyperplasia at 14 days in a rat balloon injury model. It remains unclear whether SMC integrin $\alpha_v\beta_3$ interaction with the ECM is the predominant mechanism for post-injury SMC migration and development of neointimal hyperplasia or if $\beta_1$ integrins are also important for the post-injury SMC response.

This study addresses the issue by comparing the efficacy of locally delivered linear peptide GRGDSPCA which inhibits $\beta_1$ integrins more strongly than $\beta_3$ integrin, versus cRGD, a cyclic peptide (GPenGRGDSPCA) which targets $\beta_3$ integrins, in limiting 14 d post-injury neointimal hyperplasia.

Materials and Methods

In 14 rats (male, 350 g) the left carotid artery was balloon abraded (2fr Fogarty×3). Linear (4/14 rats) or cyclic RGD (5/14) was locally applied at 1 mM to the injured artery in an adventitial Pluronic™ gel (500 μl). Untreated rats (5/14) served as controls. At 14 days rats were sacrificed, carotid arteries pressure fixed and mean intima and media thickness determined.

Results

Figure 8:
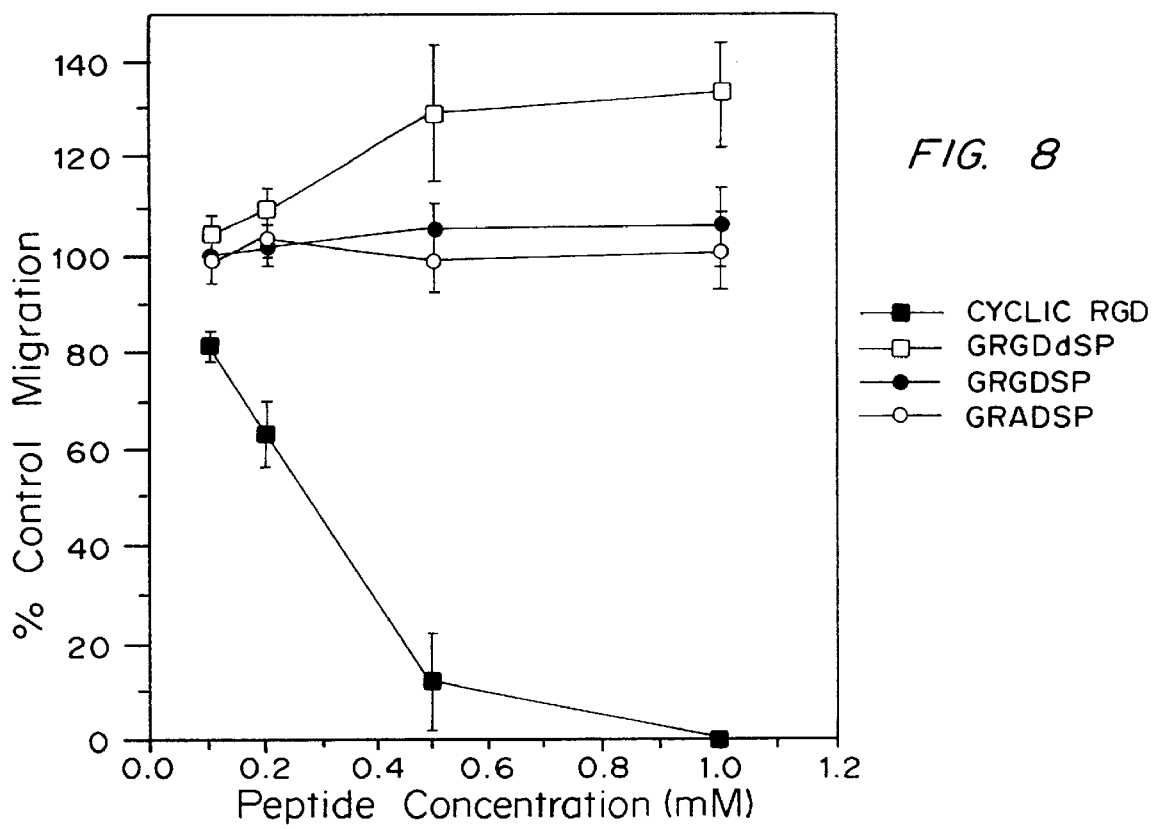
FIG. 8 is a graph of % control migration versus peptide concentration (mM) for cyclic RGD (closed squares), GRGDdSP (a stronger inhibitor of $\beta_1$ integrins) (open squares), GRGDSP (linear RGD peptide which inhibits $\beta_1$ integrins) (closed circles), and GRADSP (non-sense peptide) (open circles).

The mean intima/media ratios (I/Ms) in balloon abraded cyclic and linear RGD-treated arteries were 0.17±0.10 ($p<0.001$) and 1.95±0.32 ($p<0.007$) respectively. In control abraded arteries, the I/M was 2.09±0.54. Local application of cRGD peptide lead to a 92% reduction in the degree of hyperplasia whereas linear RGD-treatment resulted in no significant reduction. Results are shown in FIG. 8 for three linear peptides, two known $\beta_1$-integrin inhibitors, a nonsense peptide, and the cyclic RGD peptide, which were studied under similar conditions.

Discussion $\beta_3$ integrin inhibitors, such as CRGD, can effectively reduce neointimal hyperplasia development, whereas $\beta_1$ integrin inhibitors, i.e., linear RGD, fail to limit hyperplasia. Therefore, the interaction of SMC $\beta_3$ integrins with vessel wall ECM must be more important than $\beta_1$ integrin interactions for post-injury migration and subsequent development of neointimal hyperplasia. Cell integrin-matrix interactions may be an additional viable target for pharmacologic manipulation aimed at limiting injury-induced restenosis.

EXAMPLE 7

Local delivery of a non-integrin cell matrix receptor binding peptide inhibits neointimal hyperplasia following balloon injury.

The interaction of cells with the extracellular matrix protein laminin, mediated partially through a cell associated 69 kD non-integrin receptor, has been shown to regulate cell phenotype and function. Interference with this interaction via laminin peptide fragments has been shown to limit migration of neural crest cells and experimental metastasis.

Materials and Methods

In this study it was determined whether interference with laminin-69 kD receptor interactions in the arterial wall, through localized delivery of a laminin $\beta_1$ chain peptide fragment, would alter the degree of neointimal hyperplasia development at 14 days in a rat balloon injury model. In 10 rats (male, 350 g) the left carotid artery was balloon abraded (2fr. Fogarty×3). In 5/10 rats the linear nonapeptide CDPGYIGSR amid (YIGSR amide) was locally at 1 mM to the injured artery in an adventitial Pluronic™ gel (500 lambda). Untreated (5/10) served as controls. At 14 days rats were sacrificed, carotid arteries pressure fixed and mean intima and media thickness determined.

Results

The mean intima/media ratio (I/M) of control balloon abraded arteries was 2.09±0.54. In abraded YIGSR amide treated arteries the I/M ratio was 0.22±0.16 ($p<0.001$). Local application of the nonapeptide YIGSR amide lead to an 89% reduction in the degree of hyperplasia. There was no significant change in media thickness between the groups.

Discussion

The localized application of a nonapeptide fragment of the laminin $\beta_1$ chain, CDPGYIGSR amide, to the arterial wall following balloon injury modifies the normal healing response, resulting in a significant reduction in neointimal hyperplasia development. Smooth muscle cell non-integrin laminin receptor-laminin interactions may be an additional viable target for pharmacologic manipulation aimed at limiting restenosis following vascular injury.

Modifications and variations of the present invention will be obvious to those skilled in the art from the foregoing detailed description. Such modifications and variations are intended to come within the scope of the following claims.

We claim:

1. A method for altering cellular interactions on a surface, the method comprising applying a biocompatible polymeric material to a cellular or tissue surface, wherein the polymeric material is applied in a first fluent state and converted in situ to a second non-fluent state, and wherein the material in the second non-fluent state has a controlled porosity and permeability for passage therethrough of macromolecules, microorganisms, and cells, wherein the polymeric material has incorporated therein a bioactive agent which is a modulator of cellular interactions.

2. The method of claim 1 wherein the polymeric material is capable of controlled delivery of the bioactive agent.

3. The method of claim 1 wherein the polymeric material is selected from the group consisting of biodegradable and bioerodible materials.

4. The method of claim 1 wherein the polymeric material is selected from the group consisting of an organogel and a hydrogel.

5. The method of claim 1 wherein the polymer is applied to a tissue lumen surface.

6. The method of claim 1 wherein the bioactive agent is a modulator of cell-extracellular matrix interactions.

7. A method for altering cellular interactions, the method comprising applying a polymeric material to a substrate selected from the group consisting of a prosthesis, implant, and unstable plaque; wherein the polymeric material is applied in a first fluent state and converted in situ to a second non-fluent state; and wherein the material in the second non-fluent state has a controlled porosity and permeability for passage therethrough of macromolecules, microorganisms, and cells; and wherein the polymeric material has incorporated therein a bioactive agent which is a modulator of cellular interactions.

8. The method of claim 7 wherein the polymeric material is a trophic layer on the surface.

9. The method of claim 1 wherein the bioactive agent is selected from the group consisting of chemotactic agents, haptotactic agents, and contact guidance agents.

10. The method of claim 9 wherein the haptotactic agent is an extracellular matrix protein.

11. The method of claim 9 wherein the haptotactic agent is selected from the group consisting of peptides comprising the sequence RGD and peptides comprising the sequence YIGSR.

12. The method of claim 11 wherein the haptotactic peptide is a cyclic peptide containing the RGD sequence.

13. The method of claim 12 wherein the peptide is applied in the polymeric material to a blood vessel.

14. The method of claim 11 wherein the haptotactic peptide contains the sequence YIGSR.

15. The method of claim 14 wherein the peptide is applied in the polymeric material to a blood vessel.

16. The method of claim 1, in which the bioactive agent is selected from the group of consisting of macrophage chemotactic factor, basic transformation growth factor, tumor angiogenesis factor, fibroblast growth factor and epidermal growth factor, insulin-like growth factor, platelet derived growth factor, and interleukins.

17. The method of claim 6 wherein the bioactive agent is an antiproliferative and wherein the polymeric material is applied to a cancerous area.

18. The method of claim 6 wherein the polymeric material is applied to a blood vessel to provide hemocompatibility.

19. The method of claim 18 wherein the polymer is selected from the group consisting of polyoxyalkylene polymers and copolymers, copolymers and blends of polyoxyalkylenes with poly(alpha-hydroxy acids), hydroxypropyl cellulose, purified konjac glucomannan gum, agarose, agar, furcellaran, beta-carrageenan, beta-1,3-glucans, hyaluronic acid, alginates and derivatized alginates and kappa, lambda, and iota carrageenans, heparin, carboxymethyl cellulose, cellulose sulfate, xanthan gum, pectin, chitosan, and polymers of monomers containing acrylic, allylic or vinyl groups, and dimeric or oligomeric forms of these compounds such as methylene bisacrylamide.

* * * * *